United States Patent
Nelson et al.

(10) Patent No.: US 12,246,163 B2
(45) Date of Patent: Mar. 11, 2025

(54) AUTOMATIC-SEALING BALLOON-FILLING CATHETER SYSTEM

(71) Applicant: Allurion Technologies, Inc., Natick, MA (US)

(72) Inventors: David W. Nelson, Wayland, MA (US); Bruce A. Horwitz, Newton, MA (US)

(73) Assignee: Allurion Technologies, Inc., Natick, MA (US)

( * ) Notice: Subject to any disclaimer, the term of this patent is extended or adjusted under 35 U.S.C. 154(b) by 0 days.

(21) Appl. No.: 18/299,626

(22) Filed: Apr. 12, 2023

(65) Prior Publication Data

US 2024/0342366 A1    Oct. 17, 2024

(51) Int. Cl.
*A61F 5/00*      (2006.01)
*A61M 5/142*    (2006.01)
*A61M 25/10*    (2013.01)

(52) U.S. Cl.
CPC ...... *A61M 5/14276* (2013.01); *A61M 25/104* (2013.01); *A61F 5/00* (2013.01); *A61F 5/003* (2013.01); *A61F 5/0079* (2013.01)

(58) Field of Classification Search
CPC ........ A61M 25/10185; A61M 5/14276; A61M 2005/5073; A61F 5/003; A61F 5/0036; A61F 5/0043; A61F 5/0066
See application file for complete search history.

(56) References Cited

U.S. PATENT DOCUMENTS

| | | |
|---|---|---|
| 2,911,988 A | 11/1959 | Ravn |
| 3,586,018 A | 6/1971 | Bogardh et al. |
| 3,638,733 A | 2/1972 | De Rouville et al. |
| 3,853,116 A | 12/1974 | Bucalo |
| 4,133,315 A | 1/1979 | Berman et al. |

(Continued)

FOREIGN PATENT DOCUMENTS

| | | |
|---|---|---|
| CA | 2925648 | 5/2007 |
| CA | 2865056 | 8/2013 |

(Continued)

OTHER PUBLICATIONS

Stony Brook Medicine "Obalon Swallowable Balloon Capsules" Feb. 21, 2017, 2 pages. Retrieved from the Internet [Sep. 2, 2020] URL: https://www.youtube.com/watch?v=CEznWcGacLI.

*Primary Examiner* — Michael J Tsai
*Assistant Examiner* — Justin L Zamory
(74) *Attorney, Agent, or Firm* — Levine Bagade Han LLP

(57) ABSTRACT

The present invention relates to an implantable medical device comprising a device body having an internal reservoir configured to expand in size. The device can comprise an anchor structure affixed to a wall of the device body and having an interior passage, a conduit having a fill end and a device end with a conduit lumen extending therethrough, and a plug-port member comprising a shaft section opposite to a plug section, with a port section located therebetween. The device end of the conduit can be coupled to the shaft section and the plug-port member can be located within the interior passage such that in a fill configuration, the port section and the plug section are located within the internal reservoir allowing the fluid to pass from the conduit lumen into a shaft lumen, through one or more port openings in the port section and into the internal reservoir.

29 Claims, 27 Drawing Sheets

(56) References Cited

U.S. PATENT DOCUMENTS

| | | |
|---|---|---|
| 4,141,771 A | 2/1979 | Barker et al. |
| 4,253,201 A | 3/1981 | Ross et al. |
| 4,370,374 A | 1/1983 | Raabe et al. |
| 4,614,188 A | 9/1986 | Bazell et al. |
| 4,636,213 A | 1/1987 | Pakiam |
| 4,723,547 A | 2/1988 | Kullas et al. |
| 4,732,188 A | 3/1988 | Gabrlik et al. |
| 4,739,758 A | 4/1988 | Lai et al. |
| 4,842,007 A | 6/1989 | Kurtz |
| 4,899,747 A | 2/1990 | Garren et al. |
| 4,949,756 A | 8/1990 | Melinyshyn et al. |
| 5,018,665 A | 5/1991 | Sulmone |
| 5,092,847 A | 3/1992 | Pozzo |
| 5,181,921 A | 1/1993 | Makita et al. |
| 5,222,970 A | 6/1993 | Reeves |
| 5,336,123 A | 8/1994 | Laske et al. |
| 5,348,537 A | 9/1994 | Wiesner et al. |
| 5,496,203 A | 3/1996 | Murray |
| 5,507,808 A | 4/1996 | Becker |
| 5,595,521 A | 1/1997 | Becker |
| 5,632,297 A | 5/1997 | Sciullo et al. |
| 5,950,624 A | 9/1999 | Hart |
| 6,162,251 A | 12/2000 | Kredovski |
| 6,197,005 B1 | 3/2001 | Gerlach et al. |
| 6,259,953 B1 | 7/2001 | Lucchesi et al. |
| 6,367,499 B2 | 4/2002 | Taku |
| 6,375,972 B1 | 4/2002 | Guo et al. |
| 6,460,541 B1 | 10/2002 | Shah et al. |
| 6,644,336 B2 | 11/2003 | Dolan |
| 6,712,832 B2 | 3/2004 | Shah |
| 6,814,097 B2 | 11/2004 | Girouard |
| 6,939,292 B2 | 9/2005 | Mizuno et al. |
| 7,169,134 B2 | 1/2007 | Bills |
| 7,172,613 B2 | 2/2007 | Wazne |
| 7,485,093 B2 | 2/2009 | Glukhovsky |
| 7,854,745 B2 | 12/2010 | Brister et al. |
| 8,183,227 B1 | 5/2012 | Perrin et al. |
| 8,202,291 B1 | 6/2012 | Brister et al. |
| 8,282,666 B2 * | 10/2012 | Birk .............. A61F 5/0046 606/192 |
| 8,287,562 B2 | 10/2012 | Kasic, II |
| 8,292,911 B2 | 10/2012 | Brister et al. |
| 8,585,676 B2 | 11/2013 | Shah |
| 8,628,571 B1 | 1/2014 | Hacohen et al. |
| 8,740,845 B2 | 6/2014 | Shah et al. |
| 8,784,486 B2 | 7/2014 | Schuessler |
| 8,814,898 B2 | 8/2014 | Gaur et al. |
| 8,870,907 B2 | 10/2014 | Gaur et al. |
| 8,974,483 B2 | 3/2015 | Gaur et al. |
| 9,387,107 B2 | 7/2016 | Gaur et al. |
| 9,463,106 B2 | 10/2016 | Khieu et al. |
| 9,662,239 B2 | 5/2017 | Brister et al. |
| 9,827,128 B2 | 11/2017 | Brister et al. |
| 9,827,129 B2 | 11/2017 | Gaur et al. |
| 9,849,018 B2 | 12/2017 | Wecker et al. |
| 10,182,932 B2 | 1/2019 | Moss et al. |
| 10,238,516 B1 | 3/2019 | Singh et al. |
| 10,307,279 B2 | 6/2019 | Wecker et al. |
| 10,470,908 B2 | 11/2019 | Nelson et al. |
| 10,583,024 B2 | 3/2020 | Nelson et al. |
| 10,588,768 B2 | 3/2020 | Nelson et al. |
| 10,729,572 B2 | 8/2020 | Moss et al. |
| 10,786,379 B2 | 9/2020 | Gaur et al. |
| 11,098,813 B2 | 8/2021 | Nelson |
| 11,497,900 B2 | 11/2022 | Chadwick et al. |
| 11,559,418 B2 | 1/2023 | Nelson et al. |
| 11,766,346 B2 | 9/2023 | Moss et al. |
| 11,828,377 B2 | 11/2023 | Nelson |
| 2001/0018929 A1 | 9/2001 | Taku |
| 2002/0183777 A1 | 12/2002 | Shannon |
| 2002/0198470 A1 | 12/2002 | Imran et al. |
| 2003/0106583 A1 | 6/2003 | Weng |
| 2003/0171768 A1 | 9/2003 | McGhan |
| 2003/0229263 A1 | 12/2003 | Connors et al. |
| 2003/0229384 A1 | 12/2003 | Mon |
| 2004/0044353 A1 | 3/2004 | Gannoe |
| 2004/0073249 A1 | 4/2004 | Trotta |
| 2004/0101540 A1 | 5/2004 | Cooker |
| 2004/0146559 A1 | 7/2004 | Sowden et al. |
| 2004/0186502 A1 | 9/2004 | Sampson et al. |
| 2005/0027261 A1 | 2/2005 | Weaver et al. |
| 2005/0033331 A1 * | 2/2005 | Burnett .............. A61B 5/14539 606/154 |
| 2005/0055039 A1 | 3/2005 | Burnett et al. |
| 2005/0096750 A1 | 5/2005 | Kagan et al. |
| 2005/0150548 A1 | 7/2005 | Kita et al. |
| 2006/0004323 A1 | 1/2006 | Chang et al. |
| 2006/0058829 A1 | 3/2006 | Sampson et al. |
| 2006/0222705 A1 | 10/2006 | Flanner et al. |
| 2007/0010791 A1 | 1/2007 | Drechsler et al. |
| 2007/0078476 A1 | 4/2007 | Hull, Sr. et al. |
| 2007/0207199 A1 | 9/2007 | Sogin |
| 2007/0250094 A1 | 10/2007 | Makower et al. |
| 2008/0195226 A1 | 8/2008 | Williams et al. |
| 2008/0241094 A1 | 10/2008 | Burnett et al. |
| 2008/0243071 A1 | 10/2008 | Quijano et al. |
| 2008/0249635 A1 | 10/2008 | Weitzner et al. |
| 2008/0269555 A1 | 10/2008 | Paganon et al. |
| 2008/0276992 A1 | 11/2008 | Nomichi et al. |
| 2008/0306441 A1 | 12/2008 | Brown et al. |
| 2009/0024227 A1 | 1/2009 | Lesh |
| 2009/0048684 A1 | 2/2009 | Lesh |
| 2009/0118756 A1 | 5/2009 | Valencon |
| 2009/0192535 A1 | 7/2009 | Kasic |
| 2009/0259246 A1 | 10/2009 | Eskaros et al. |
| 2009/0275919 A1 | 11/2009 | Todd et al. |
| 2009/0277515 A1 | 11/2009 | Pechtold |
| 2009/0299327 A1 | 12/2009 | Tilson et al. |
| 2010/0062057 A1 | 3/2010 | Berge et al. |
| 2010/0100116 A1 | 4/2010 | Brister et al. |
| 2010/0110311 A1 | 5/2010 | Sade et al. |
| 2010/0114311 A1 | 5/2010 | Becker |
| 2010/0121224 A1 | 5/2010 | Toyota et al. |
| 2010/0137897 A1 | 6/2010 | Brister et al. |
| 2010/0168511 A1 | 7/2010 | Muni et al. |
| 2010/0174307 A1 | 7/2010 | Birk |
| 2010/0193050 A1 | 8/2010 | Job |
| 2010/0243065 A1 | 9/2010 | Zweber |
| 2010/0246165 A1 | 9/2010 | Diaz et al. |
| 2010/0274194 A1 | 10/2010 | Sobelman et al. |
| 2011/0004236 A1 | 1/2011 | Priplata et al. |
| 2011/0112383 A1 | 5/2011 | Voss et al. |
| 2011/0275882 A1 | 11/2011 | Hutzenlaub et al. |
| 2012/0141544 A1 | 6/2012 | Fuisz et al. |
| 2012/0141545 A1 | 6/2012 | Fuisz et al. |
| 2012/0232576 A1 | 9/2012 | Brister et al. |
| 2012/0273050 A1 | 11/2012 | Metzger et al. |
| 2013/0012980 A1 | 1/2013 | Brister et al. |
| 2013/0035711 A1 | 2/2013 | Schwab et al. |
| 2013/0165873 A1 | 6/2013 | Morriss et al. |
| 2013/0190796 A1 | 7/2013 | Tilson et al. |
| 2013/0218190 A1 | 8/2013 | Gaur et al. |
| 2013/0267984 A1 | 10/2013 | Gaur et al. |
| 2013/0289604 A1 | 10/2013 | Brister et al. |
| 2013/0296751 A1 | 11/2013 | Martin et al. |
| 2014/0012363 A1 | 1/2014 | Franano et al. |
| 2014/0066967 A1 | 3/2014 | Levy et al. |
| 2014/0074142 A1 | 3/2014 | Khieu et al. |
| 2014/0180252 A1 | 6/2014 | Gabriel |
| 2014/0188151 A1 | 7/2014 | Gaur et al. |
| 2014/0296903 A1 | 10/2014 | Gaur et al. |
| 2015/0196408 A1 | 7/2015 | Moss et al. |
| 2015/0305746 A1 | 10/2015 | Johnson et al. |
| 2016/0010758 A1 | 1/2016 | Nomichi et al. |
| 2016/0045719 A1 | 2/2016 | Ha et al. |
| 2016/0109029 A1 | 4/2016 | Dulin |
| 2016/0278957 A1 | 9/2016 | Gaur et al. |
| 2017/0211715 A1 | 7/2017 | Balmaceda et al. |
| 2017/0312111 A1 | 11/2017 | Sharma et al. |
| 2018/0042747 A1 | 2/2018 | Gaur et al. |
| 2018/0071127 A1 | 3/2018 | Wecker et al. |
| 2018/0236203 A1 | 8/2018 | Franklin et al. |
| 2018/0311484 A1 | 11/2018 | Lake et al. |
| 2018/0344498 A1 | 12/2018 | Moss et al. |

(56) References Cited

U.S. PATENT DOCUMENTS

| | | |
|---|---|---|
| 2019/0076152 A1 | 3/2019 | Franklin et al. |
| 2019/0262157 A1* | 8/2019 | Nelson .................... A61F 5/003 |
| 2019/0388258 A1 | 12/2019 | Nelson et al. |
| 2019/0388259 A1 | 12/2019 | Nelson et al. |
| 2020/0011442 A1 | 1/2020 | Nelson |
| 2020/0155335 A1 | 5/2020 | Nelson et al. |
| 2020/0188644 A1 | 6/2020 | Chadwick et al. |
| 2020/0323672 A1 | 10/2020 | Moss et al. |
| 2021/0341069 A1 | 11/2021 | Nelson |
| 2023/0120118 A1 | 4/2023 | Nelson et al. |
| 2024/0041628 A1 | 2/2024 | Moss et al. |
| 2024/0084908 A1 | 3/2024 | Nelson |

FOREIGN PATENT DOCUMENTS

| | | |
|---|---|---|
| CN | 1387418 | 12/2002 |
| CN | 101384231 | 3/2009 |
| CN | 201977967 | 9/2011 |
| CN | 102883684 | 1/2013 |
| CN | 106029013 | 10/2016 |
| EP | 2139439 | 1/2010 |
| EP | 2817062 | 12/2014 |
| EP | 3117865 | 1/2017 |
| EP | 3720395 | 10/2020 |
| GB | 201514322 | 9/2015 |
| JP | 2008-513132 | 5/2008 |
| JP | 2008-515464 | 5/2008 |
| JP | 2010-523280 | 7/2010 |
| JP | 2011-517611 | 6/2011 |
| JP | 2016-030000 | 3/2016 |
| WO | WO 2000/012167 | 3/2000 |
| WO | WO 2004/075795 | 9/2004 |
| WO | WO 2006/020929 | 2/2006 |
| WO | WO 2009/059802 | 5/2009 |
| WO | WO 2009/059803 | 5/2009 |
| WO | WO 2011/106157 | 9/2011 |
| WO | WO 2013/126593 | 8/2013 |
| WO | WO 2014/074625 | 5/2014 |
| WO | WO 2015/066545 | 5/2015 |
| WO | WO 2016/145076 | 9/2016 |
| WO | WO 2017/136840 | 8/2017 |
| WO | WO 2018/142761 | 8/2018 |
| WO | WO 2019/112768 | 6/2019 |
| WO | WO 2019/165449 | 8/2019 |
| WO | WO 2020/010359 | 1/2020 |
| WO | WO 2020/123916 | 6/2020 |

* cited by examiner

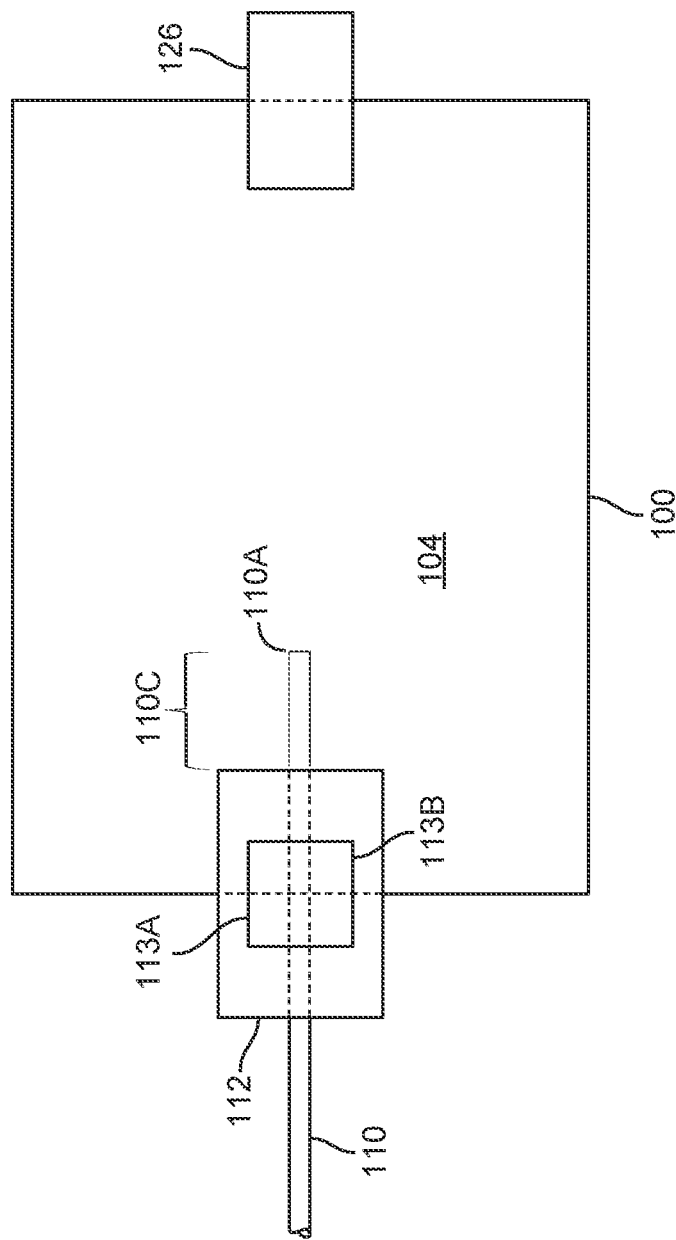

AUTOMATIC-SEALING BALLOON-FILLING CATHETER SYSTEM

BACKGROUND OF THE INVENTION

The present invention generally relates to the field of balloon devices that occupy spaces within remote cavities and more particularly relates to the catheters/conduits used to inflate these devices with fluid.

One example of balloon devices that occupy space in a remote cavity is an intragastric balloon for weight loss. According to 2010 World Health Organization data, 198 million Americans over the age of 15 are above target weight. Of these individuals, 89 million are considered overweight (25<Body Mass Index<30) and 109 million are considered obese (Body Mass Index>30). Worldwide, more than 1.4 billion adults age 20 and over are overweight, and 500 million are obese. Obesity places patients at increased risk of numerous, potentially disabling conditions including type 2 diabetes, heart disease, stroke, gallbladder disease, and musculoskeletal disorders. Compared with healthy-weight adults, obese adults are more than three times as likely to have been diagnosed with diabetes or high blood pressure. In the United States it is estimated that one in five cancer-related deaths may be attributable to obesity in female non-smokers and one in seven among male non-smokers
(>=50 years of age). On average, men and women who were obese at age 40 live 5.8 and 7.1 fewer years, respectively, than their healthy-weight peers.

For the vast majority of the overweight and obese population for whom surgical obesity procedures are not appropriate, few efficacious and affordable interventions are currently available. Diet and exercise remain the front line approaches to obesity, however this approach has at best slowed the growth of the epidemic. To date, drug therapies have dose limiting side effects or have lacked meaningful long-term efficacy.

One less-invasive intervention that has begun to gain popularity is an intragastric balloon. Intragastric balloons in their uninflated state can be placed endoscopically or positioned using other methods and, once in place, are typically filled with a filling fluid through a thin catheter or conduit extending up the esophagus from the device in the stomach to an external fluid supply. This catheter is then removed from the device and extracted from the body through the esophagus. Upon removal of the catheter, the catheter fill system must seal the fluid communication between the interior of the device and the gastric environment to maintain the balloon in its filled state for the proscribed time.

Several approaches to sealing the catheter system have been developed. For example, in US2013/0012980 Brister describes the use of a septum, or rubber-like plug, through which a filling needle is disposed. Upon removal of the needle the rubber-like material elastically closes the puncture. While such a system is well-accepted for inflating athletic equipment such as footballs, it does require the hard, rubber-like septum to remain in the intragastric balloon for the life of the balloon.

Another approach for use in breast implants has been disclosed by Becker in US2010/0110311 in which a filling tube comprising a soft, flexible hollow tube portion and a barbed, solid distal portion is pre-installed through a piece of "semi-rigid tube" that penetrates the balloon wall. The filling tube has an outer dimension that is slightly larger than the inner dimension of the semirigid tube and is stretchable longitudinally to reduce the outer diameter to facilitate passage through the passageway in the semirigid tube. Supposedly, the outer diameter of the solid portion of the filling tube can be reduced by said longitudinal stretching to allow the solid portion to be pulled into the semi-rigid tube. The solid portion then sealingly engages the semirigid tube upon relaxation thereof. The significant force that must be applied to the filling tube to pull the solid portion into the semirigid tube apparently requires that the semirigid tube is attached to the balloon wall by a reinforcing disk of material. However, this construction prevents the balloon described by Becker from being compacted into an ingestible capsule when uninflated. The inventor further notes that expansion of the solid portion upon relaxation is not adequate to ensure the solid portion remains in the semirigid portion and that "A key element in the . . . invention resides in means such as a plurality of reverse barbs for preventing a plug valve from being dislodged . . . "

Commonly assigned publication US2013/0218190, discloses a self-scaling tunnel valve comprising two layers of thin film material through which a flexible fill catheter is disposed. The two layers tend to close together upon catheter withdrawal. This tunnel valve is extremely soft and flexible, making it suitable for compaction into an ingestible capsule for long term residence in the stomach.

It would be desirable to have a self-sealing valve that is small and/or soft enough to be compacted into an ingestible capsule while also providing a distinct sealed condition.

SUMMARY OF THE INVENTION

The present invention relates to an implantable medical device comprising a device body having an internal reservoir and configured to expand in size upon delivery of a fluid into the internal reservoir. The device can further comprise an anchor structure affixed to a wall of the device body and having an interior passage, a conduit having a fill end and a device end with a conduit lumen extending therethrough, and a plug-port member comprising a shaft section opposite to a plug section, with a port section located therebetween.

The shaft section can comprise a shaft lumen in fluid communication with the port section. The device end of the conduit can be coupled to the shaft section and the plug-port member can be located within the interior passage such that in a fill configuration, the port section and the plug section are located within the internal reservoir allowing the fluid to pass from the conduit lumen into the shaft lumen, through one or more port openings in the port section and into the internal reservoir.

The plug-port member can comprise a weakened section adjacent to the plug section. wherein pulling the fill end of the conduit applies a pulling force on the shaft section such that once the pulling force exceeds a frictional resistance force between the plug-port member and the anchor structure, the plug-port member seats into the anchor structure such that the port section is no longer in fluid communication with the internal reservoir, wherein once seated into the anchor structure, continued application of the pulling force causes detachment of the shaft section from the plug section at the weakened section to permit detachment of the conduit from the device body.

The anchor structure can be located interior and/or exterior to the internal reservoir. The shaft section can be located completely interior to the interior reservoir or at least in part exterior to the internal reservoir. The plug-port member can comprise a higher elastic modulus than an elastic modulus of the conduit such that the conduit stretches during application of the pulling force prior to the pulling force exceeding the frictional resistance force to store an energy to seat the plug-port member into the anchor structure while the device body is restrained. The conduit can be inelastic and transmits a pulling force to seat the plug-port member into the anchor structure while the device body is restrained.

The weakened section can be between the device end and the one or more port openings. The weakened section can be formed at the one or more port openings. The weakened section can be between the fill end and the one or more port openings. A radiopaque marker can be positioned concentric to the anchor structure. The plug-port member can be monolithic.

In another variation, a valve assembly for use with an expandable device body can be provided, comprising an anchor structure affixed to a wall of the device body and having an interior passage. The assembly can further comprise a conduit having a fill end and a device end with a conduit lumen extending therethrough and a plug-port member comprising a shaft section opposite to a plug section, with a port section located therebetween. The shaft section can comprise a shaft lumen in fluid communication with the port section, where the device end of the conduit is coupled to the shaft section and where the plug-port member is located within the interior passage such that in a fill configuration, the port section and the plug section are located within an internal reservoir of the expandable device body allowing the fluid to pass from conduit lumen into the shaft lumen, through one or more port openings in the port section and into the internal reservoir.

The plug-port member can comprise a weakened section adjacent to the plug section, wherein pulling the fill end of the conduit applies a pulling force on the shaft section such that once the pulling force exceeds a frictional resistance force between the plug-port member and the anchor structure, the plug-port member seats into the anchor structure such that the port section is no longer in fluid communication with the internal reservoir, wherein once seated into the anchor structure, continued application of the pulling force causes detachment of the shaft section from the plug section at the weakened section to permit detachment of the conduit from the expandable device body.

The anchor structure can be located interior and/or exterior to the internal reservoir. A portion of the anchor structure can be exterior to the device body. The assembly can further comprise a sealing ring positioned inside the interior passage. The plug-port member can comprise a higher modulus than a modulus of the conduit such that the conduit stretches during application of the pulling force to store an energy to seat the plug-port member into the anchor structure while the device body is restrained. The conduit can be configured to stretch during application of the pulling force, where the stretching of the conduit builds a force to seat the plug-port member into the anchor structure while the device body is restrained. The weakened section can be between the device end and the one or more port openings. The weakened section can be formed at the one or more port openings. The weakened section can be between the fill end and the one or more port openings. A radiopaque marker can be positioned concentric to the plug-port member at the plug section.

In another variation, an implantable medical device can be provided comprising a device body having an internal reservoir and configured to expand in size upon delivery of a fluid into the internal reservoir, an anchor structure affixed to a wall of the device body and having an interior passage, a conduit having a fill end and a device end with a conduit lumen extending therethrough, and a plug-port member comprising a shaft section opposite to a plug section, with a port section located therebetween. The shaft section can comprise a shaft lumen in fluid communication with the port section, where the device end of the conduit is coupled to the shaft section and where the plug-port member is located within the interior passage such that in a fill configuration, the port section and the plug section are located within the internal reservoir allowing the fluid to pass from the conduit lumen into the shaft lumen, through one or more port openings in the port section and into the internal reservoir. The device end of the conduit can comprise a weakened section, the weakened section dividing the device end of the conduit into a residual section and a removable section, the residual section disposed adjacent to the shaft section, wherein pulling the fill end of the conduit causes detachment of the removable section from the residual section at the weakened section to permit detachment of the conduit from the device body. After detachment of the conduit, the residual section is entirely within the anchor structure. The weakened section can be between the fill end and the port section.

In another variation, an implantable medical device can be provided comprising a device body having an internal reservoir and configured to expand in size upon delivery of a fluid into the internal reservoir, an anchor structure affixed to a wall of the device body and having an interior passage, a conduit having a fill end and a device end with a conduit lumen extending therethrough, and a plug-port member comprising a shaft section opposite to a plug section, with a port section located therebetween. The shaft section can comprise a shaft lumen in fluid communication with the port section, where the device end of the conduit is coupled to the shaft section and where the plug-port member is located within the interior passage such that in a fill configuration, the port section and the plug section are located within the internal reservoir allowing the fluid to pass from the conduit lumen into the shaft lumen, through one or more port openings in the port section and into the internal reservoir. The device can further comprise a weakened section located between the fill end and the plug section, wherein pulling the fill end of the conduit causes breaking of the weakened section. The weakened section can be on the shaft section of the plug-port member or on the conduit.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

The foregoing and other objects, features and advantages of the methods, devices, and systems described herein will become apparent from the following description in conjunction with the accompanying drawings, in which reference characters refer to the same parts throughout the different views. The drawings are not necessarily to scale; emphasis has instead been placed upon illustrating the principles of the invention. Of the drawings:

FIG. 1A is a schematic block diagram of a fluid fillable balloon device.

DETAILED DESCRIPTION OF THE INVENTION

The following illustrations are examples of the invention described herein. It is contemplated that combinations of aspects of specific embodiments or combinations of the specific embodiments themselves are within the scope of this disclosure. The methods, devices, and systems described herein can be used to improve balloon devices to be used in the stomach or any other remote cavity. However, the devices, methods, and systems of the present disclosure can also be useful in other medical and non-medical applications that require a fluid-filled device in a remote location with a removable filling system.

Figure 1B:
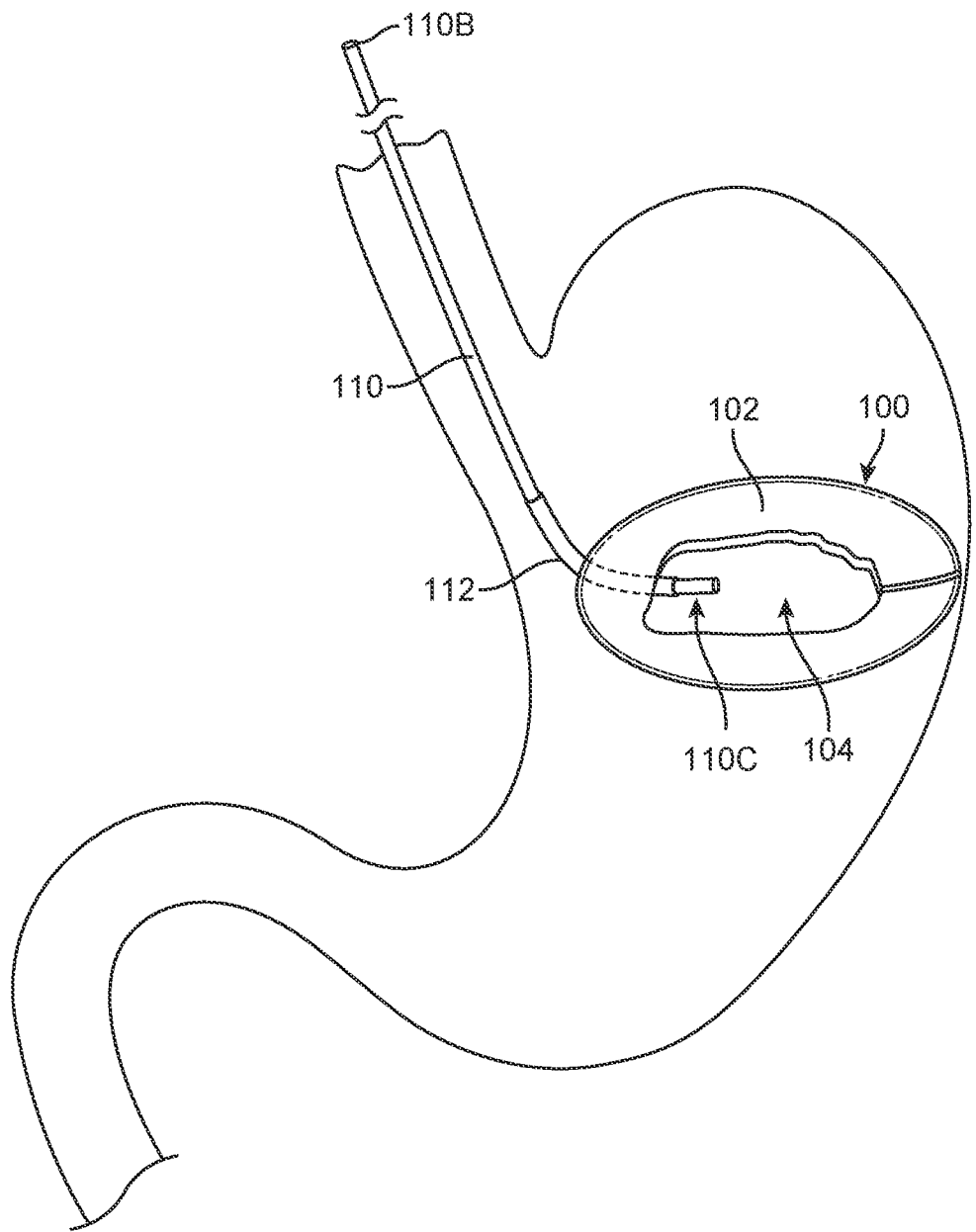
FIG. 1B illustrates a fluid fillable balloon device being filled.

FIG. 1A illustrates a schematic block diagram of a fluid fillable balloon device 100, in particular, a balloon device assembly. FIG. 1B is an illustration of device 100 in place in a patient's stomach. The device generally comprises two states of interest: a pre-deployment or uninflated configuration and a deployed, inflated or active configuration; the deployed configuration is shown. Generally, the device is inflated with a fluid. For example, the fluid can be delivered through a catheter 110 also referred to herein as a catheter or conduit, wherein the tube may pass through a lumen in the wall of the balloon device or is coupled to a fluid path 112 between the exterior and the interior of the balloon device. In alternative variations, the fluid can be delivered using any type of device that can deliver fluid. In many balloon devices, a wall 102 of the device 100 is fabricated from a thin film material such as, for example, polyurethane. In some variations the catheter 110 comprises a valve section 110C that extends through fluid path 112 into the central enclosed space or reservoir 104 of device 100. In other variations valve section 110C stops before entering the reservoir or is just adjacent to the reservoir 104. The catheter 110 is removed from the device once inflation is completed. When the conduit is removed, fluid path 112 must be sealed to prevent the fluid from leaking out through fluid path 112 from reservoir 104. As shown schematically in FIG. 1A, sealing is accomplished by fill valve, which may comprise an internal section 113B, an external section 113A, or a combination of both. In some variations, elements of the fill valve 113 may have components installed inside catheter 110 as well as in fluid path 112. Device 100 can be at a device end 110A of the catheter 110, opposite a fill end 110B of the catheter 110, which can extend out from the mouth of a patient, for example.

Figure 2A:
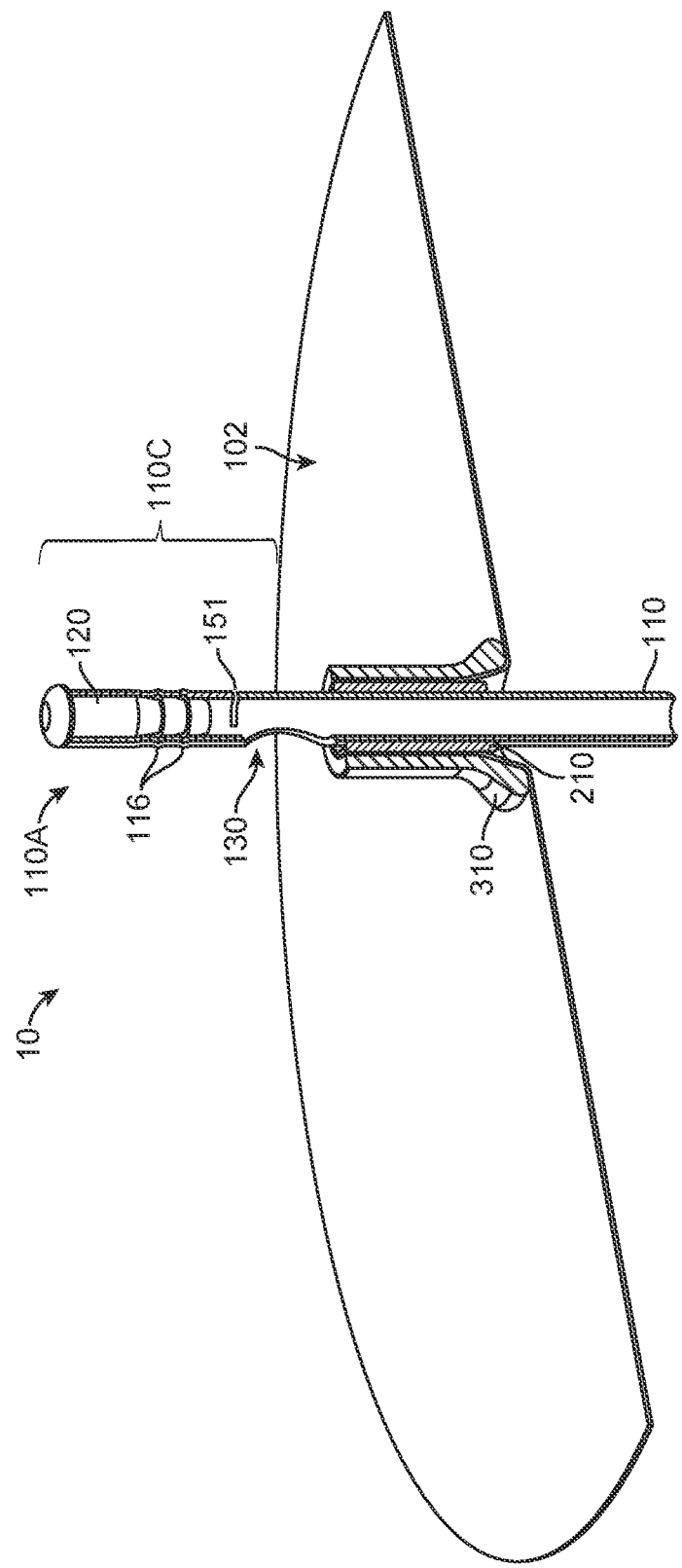
FIG. 2A is a cutaway view of a variation of an Automatic-Sealing Catheter Assembly ("ASCA") installed in a thin film wall of a balloon device.

Some variations of the device 100 further comprise a fluid release valve 126. In some variations release valve 126 is independent from fill valve 113. However, in some variations, release valve 126 may be combined, at least in part, with fill valve 113. In some variations, release valve 126 reverses the operation of the sealing mechanism of fill valve 113. In some variations, the fluid path itself serves as the fill valve, wherein the fluid path itself closes down to prevent fluid from escaping from reservoir 104. In other variations the fluid path is sealed by an automatic-sealing catheter assembly (ASCA) 10, which is a separate valve mechanism installed in the fluid path or in a portion of the conduit left behind in the fluid path when the main length of the conduit is withdrawn from the patient's body. FIG. 2A illustrates a partial cut-away view of one variation of the device 100 in the region of fill valve as it might appear within a patient's stomach, ready to be inflated. In this variation, the fill valve is an ASCA 10. The variation shown in FIG. 2A includes a catheter 110 that extends from valve section 110C to outside of device 100, typically extending far enough to reach the exterior of the patient, where the balloon thin film wall 102 defines the division between the interior and the exterior of the device.

Figure 2B:
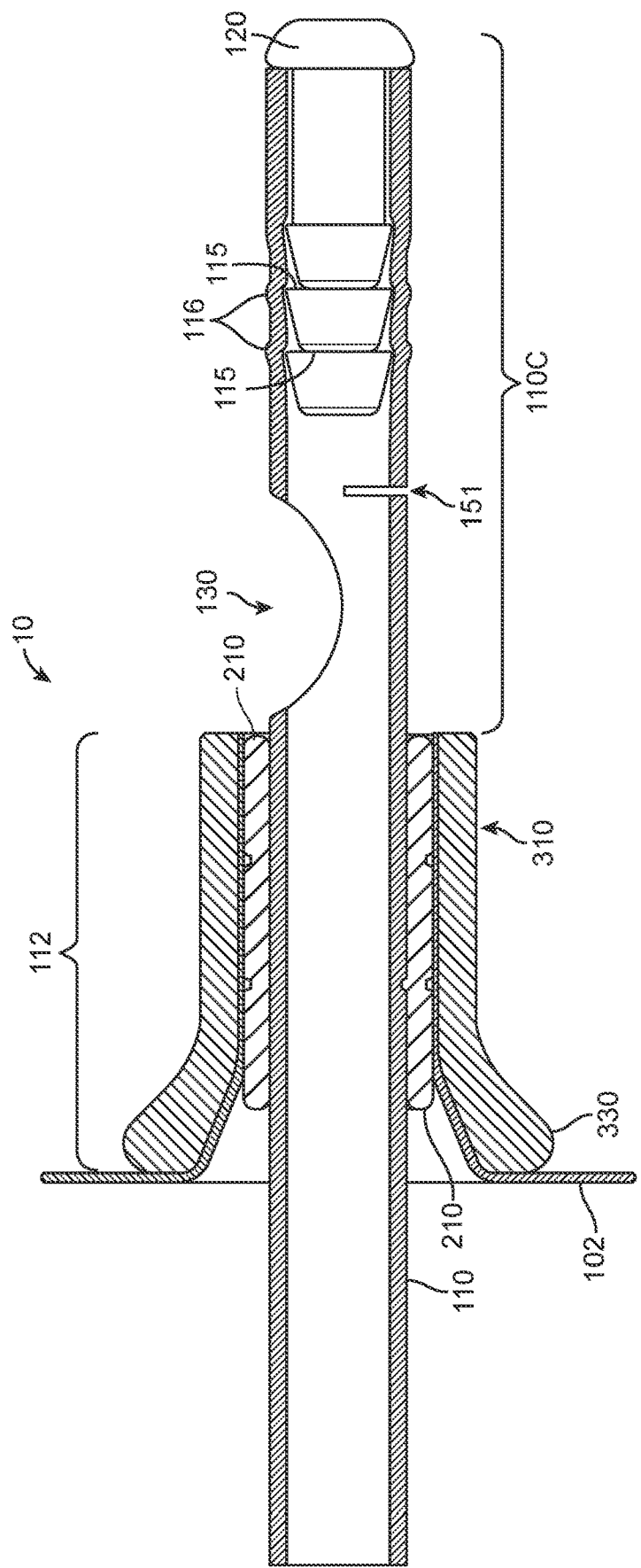
FIG. 2B is a close up view of the ASCA of FIG. 2A

FIG. 2B is a sectional view of the ASCA 10 of FIG. 2A. The assembly comprises the valve section 110C of catheter 110, the end of which has been sealed shut with a plug 120, in this variation by a toothed plug 120, during assembly. The plug has one or more circumferential, or partially circumferential, teeth or projections 115 which create rings or bulges 116 that cause an increased diameter on the exterior of valve section 110C. The circumferential projections 115 also work to lock plug 120 into section 110C substantially permanently, although glue, welding, or other bonding approaches could be used to lock a plug into section 110C. The catheter further comprises one or more side-wall openings or fill ports 130, where the variation with one fill port is shown in the figures, wherein the fill ports are disposed to be clear from plug 120 to allow filling fluid coming through the catheter to freely enter the balloon. In the illustrated variation, a catheter jacket 210 can be inserted through a section of balloon wall 102 from the exterior of the balloon and is held in place by pinching balloon wall 102 between the exterior of catheter jacket 210 and the interior of a balloon wall anchor 310. The combination of balloon wall anchor 310 and catheter jacket 210 form fluid path 112 in this variation. In the illustrated variation, the catheter further comprises a weakened section 151 designed to define where and with what tension the catheter will tear apart. In one variation, section 151 is a slit extending part way across catheter 110.

Figure 2C:
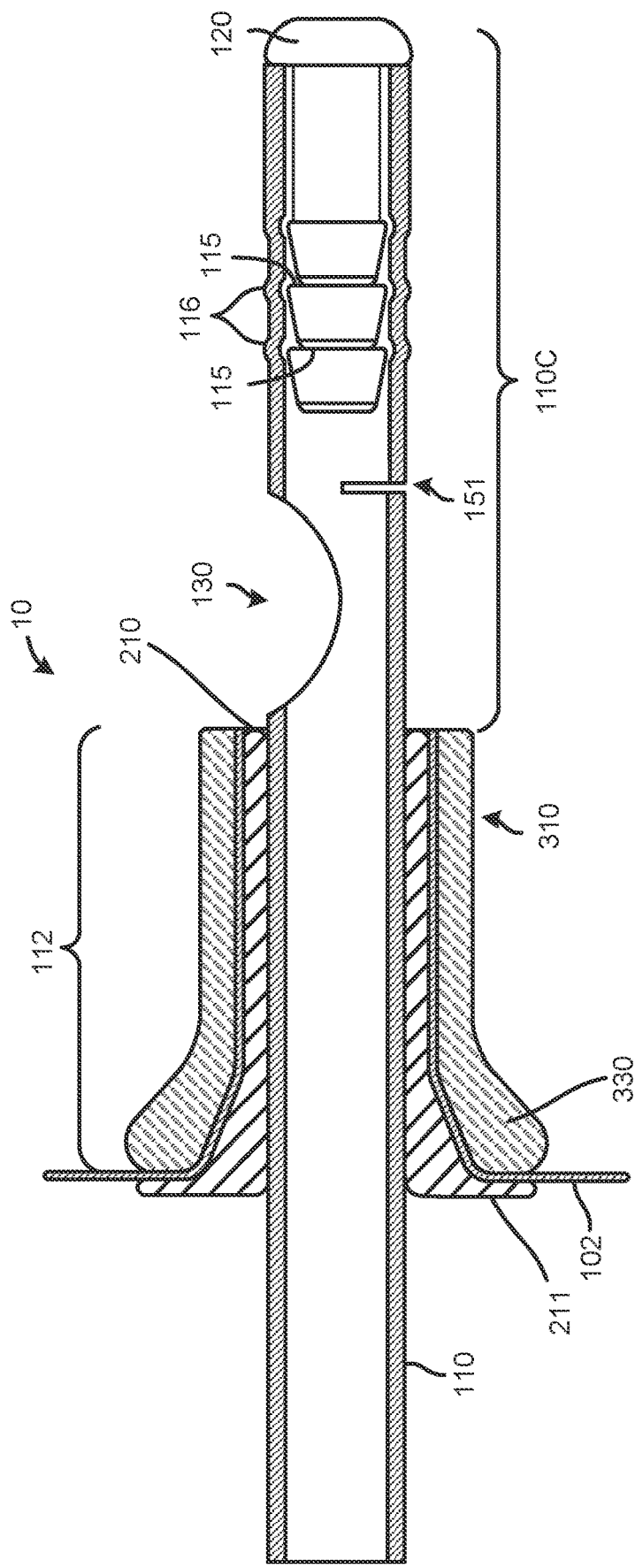
FIG. 2C is a close up view of another variation of an ASCA.

FIG. 2C is a sectional view of another variation of the ASCA 10 of FIG. 2A. In this variation, a flange portion 211 of the catheter jacket 210 can be exterior to the device body. The flange portion 211 can straddle and span the wall 102 similar to a grommet-like assembly. The flange portion 211 can be made thin and can be tapered to be gentle on the patient's stomach when the device is implanted.

Figure 3A:
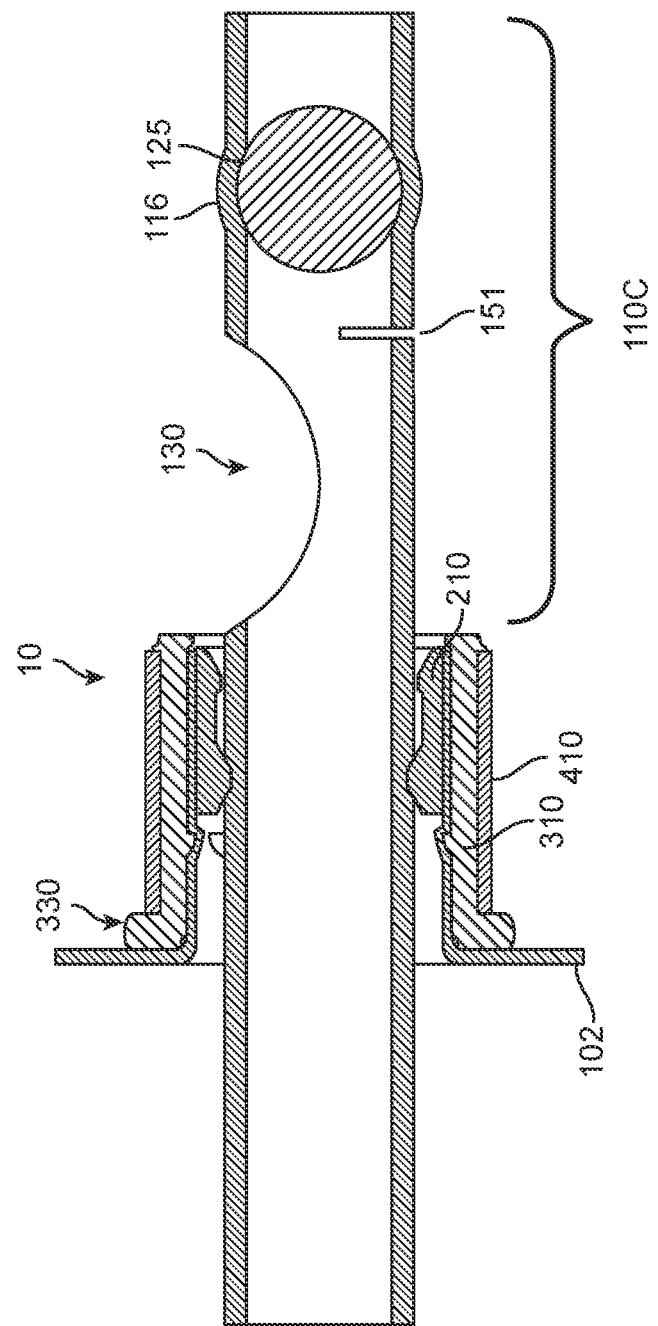
FIG. 3A is a sectional view of another variation of an ASCA.
Figure 3B:
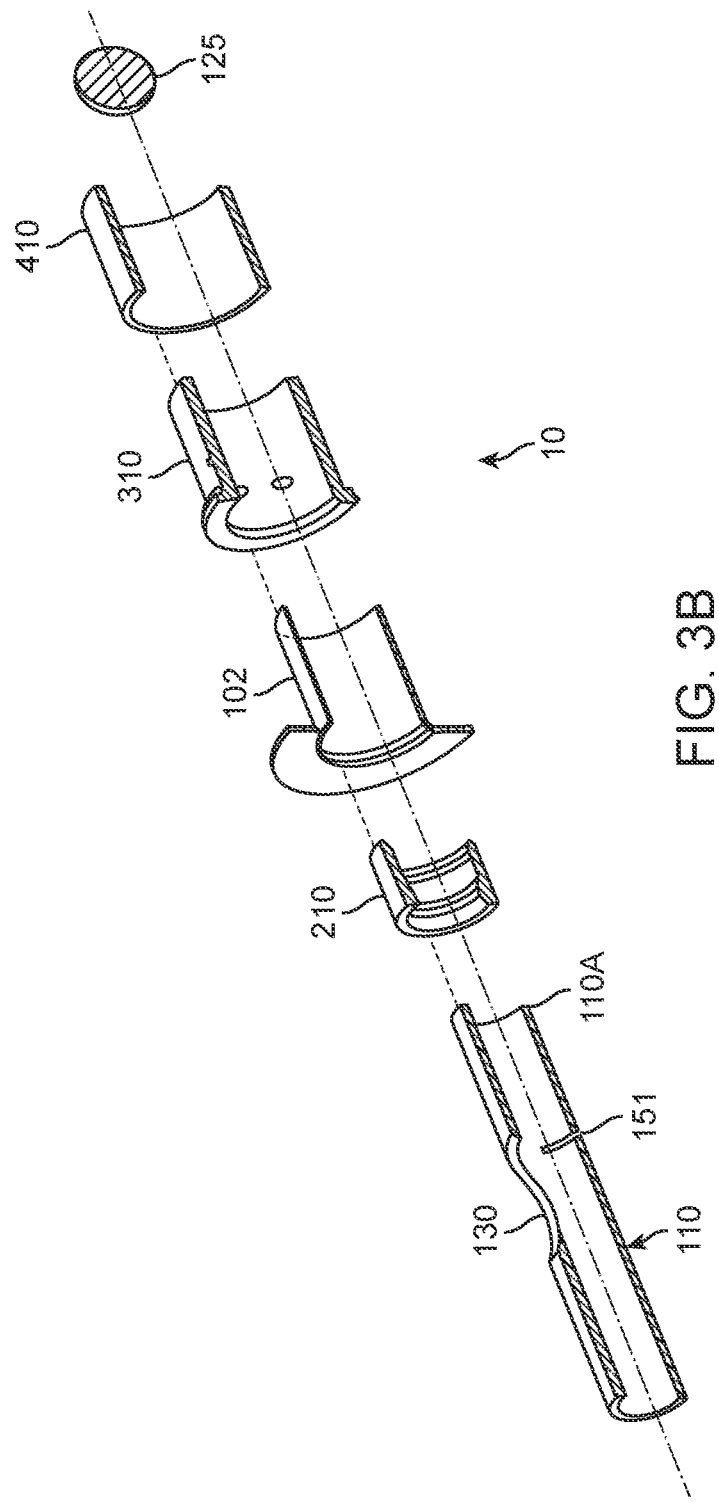
FIG. 3B is an exploded sectional view of the variation of an ASCA of FIG. 3A.

The cross-sectional view in FIG. 3A illustrates another variation of ASCA 10. In this variation, the toothed plug 120 has been replaced with a spherical plug 125, for example a ball bearing. Also, in this variation an optional retaining ring 410 has been added to reinforce wall anchor 310. An exploded, cross-sectional view of the ASCA 10 of FIG. 3A is illustrated in FIG. 3B for clarity. Balloon wall 102 can be a thin, flexible membrane that can be stretched into a structure when catheter jacket 210 is inserted into balloon wall anchor 310 and the resulting drum head of membrane can be removed to form the required open fluid path.

Figure 3C:
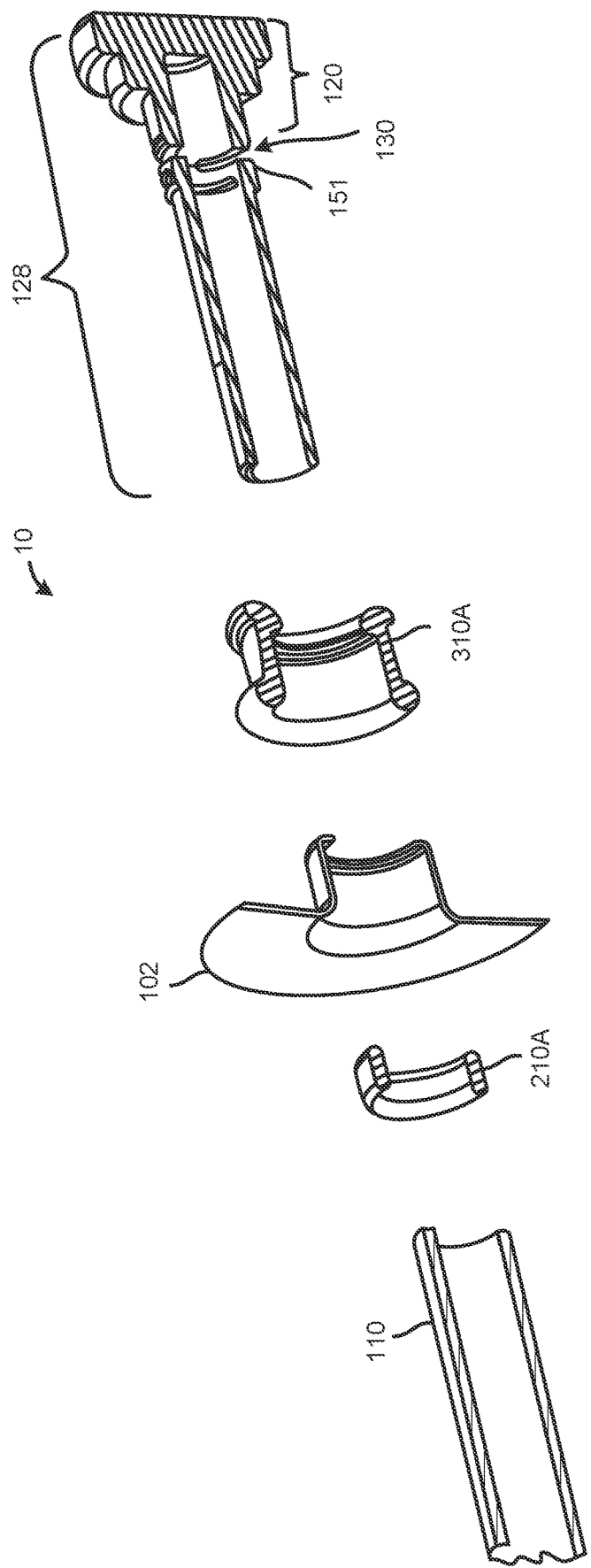
FIG. 3C is an exploded section view of another variation of an ASCA.

Another variation of ASCA 10 is illustrated in the exploded view of FIG. 3C. Catheter 110 passes through a sealing ring 210A, and the balloon wall anchor 310A, to terminate at a plug-port member 128. As shown, thin-film balloon wall 102 is trapped between the exterior of sealing ring 210A and the interior of anchor 310A. An optional radiopaque marker ring, not illustrated, may be installed around anchor 310A. The plug-port member 128 can integrate the plug 120 at the end of the catheter, the catheter fill ports 130, and the weakened section 151 of previous variations. This variation and its components will be discussed in more detail below.

Figure 4A:
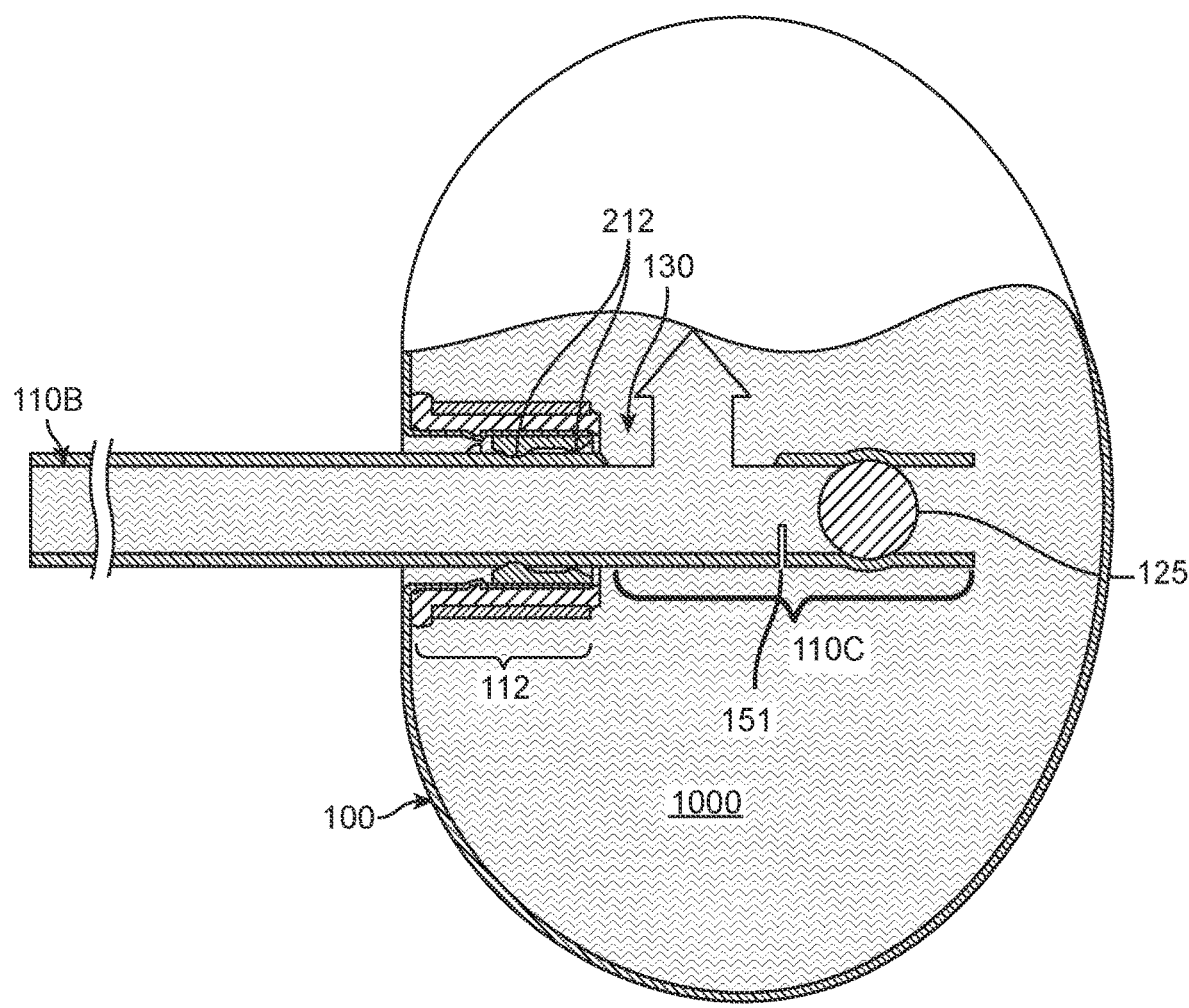
FIG. 4A is a sectional view of the variation of an ASCA of FIG. 3A while a balloon is being filled.

FIG. 4A illustrates an example of the automatic-sealing behavior of an ASCA using the ASCA of FIG. 3A as an example. FIG. 4A illustrates ASCA 10 as fluid enters a balloon device 100. As has been discussed above, device 100 is inflated by injecting a fluid 1000 at the catheter fill end 110B. The fluid travels the length of the catheter and exits the catheter through a catheter fill port 130 disposed in catheter valve section 110C, where catheter valve section 110C is intended to be inserted far enough into the balloon such that the fill port 130 is completely unobstructed by the other components of the ASCA 10. Of course, if this condition is not met the balloon will still inflate if at least a portion of the port is unobstructed, albeit at a slower rate. After a prescribed volume of fluid has been injected into the balloon, or, alternatively, a prescribed back pressure of the fluid has been reached, catheter 110 is withdrawn from the patient. However, to maintain inflation of the device 100, fluid path 112, which normally would allow two-way fluid flow, must prevent exit of the fluid to prevent deflation of the balloon.

Figure 4B:
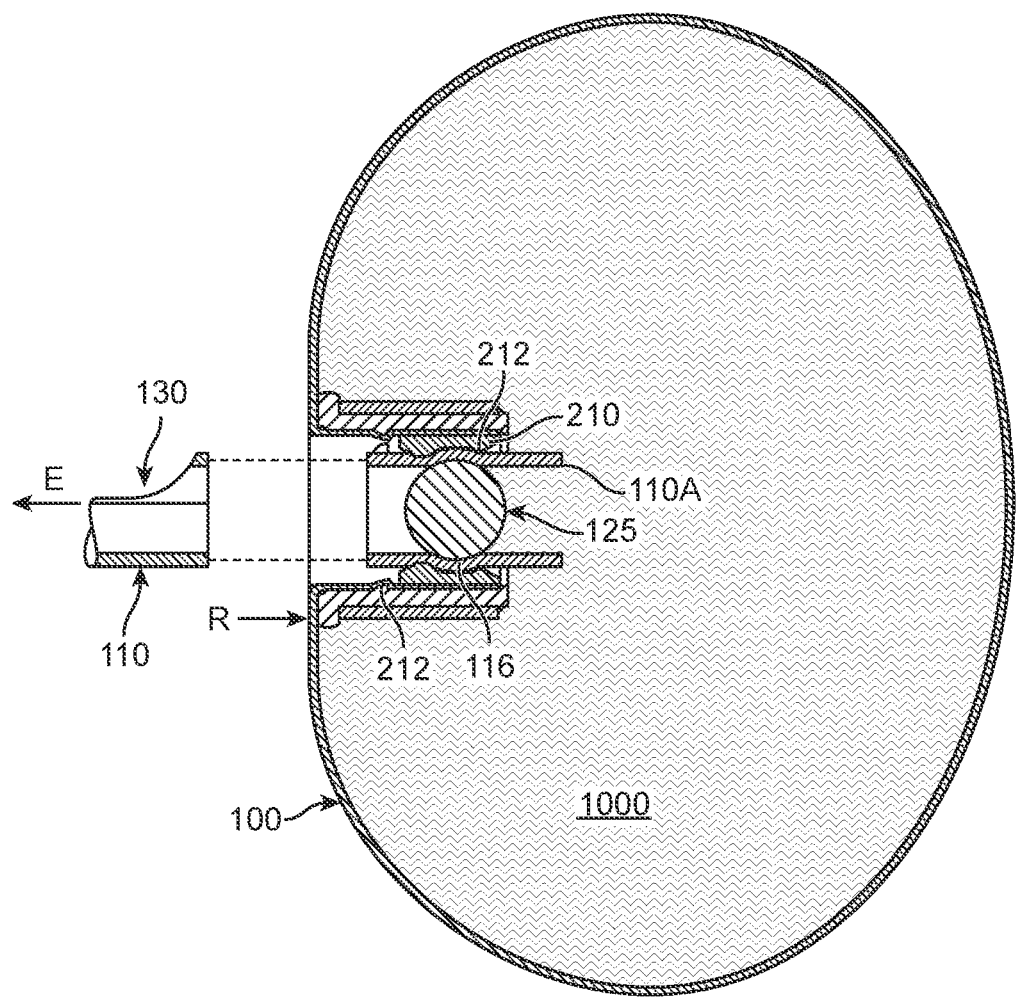
FIG. 4B is a sectional view of the ASCA of FIG. 4A in its sealed configuration after a balloon is released.

FIG. 4B illustrates a partially withdrawn catheter 110 with catheter valve section 110C in a sealing position. An extractive force, arrow E, has been applied to catheter 110 at or near catheter fill end 110B and transmitted along the catheter to the device 100. Filled device 100 was pulled by the extractive force until device 100 abuts a resistive area such as a wall of an internal organ, not shown. The resistive area provides a reaction force, arrow R, that stops the motion of device 100 so extractive force E pulls catheter valve section 110C into catheter jacket 210 until it moves spherical plug 125 between the engagement elements 212 built into the inner surface of jacket 210. In the illustrated variation, catheter valve section 110C is secured in the sealing position when catheter wall bulges 116 formed by spherical plug 125 abut engagement elements 212, which, in this variation, are ridges in the inside of catheter jacket 210. In this configuration the fill port 130 is no longer in fluid communication with the interior of the balloon and the exterior of the catheter is compressed between the internal ridges and the plug, in this case operating like an o-ring, effectively sealing the catheter assembly. Once the catheter valve section 110C has been secured in the catheter jacket, further axial tension on the catheter is applied to tear the catheter to allow the majority of the length of catheter 110 to be extracted from the patient while leaving the plugged portion of catheter valve section 110C in catheter jacket 210, as indicated in FIG. 4B. By design, tear-away weakened section 151 (shown in FIG. 4B) can be a slit that creates a unique location at which the catheter will tear; additionally, by design, the force at which the catheter tears can be adjusted to any reasonable value by varying the depth or shape of weakened section 151.

Figure 5A:
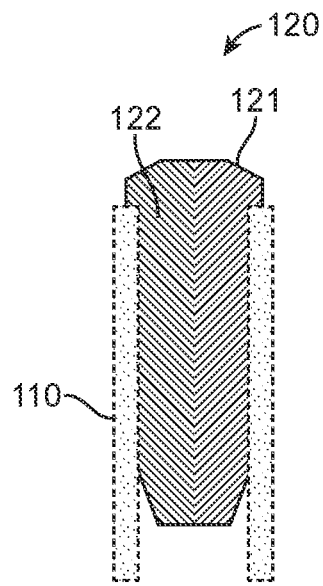
FIGS. 5A-5G illustrate variations of a plug for an ASCA.
Figure 5B:
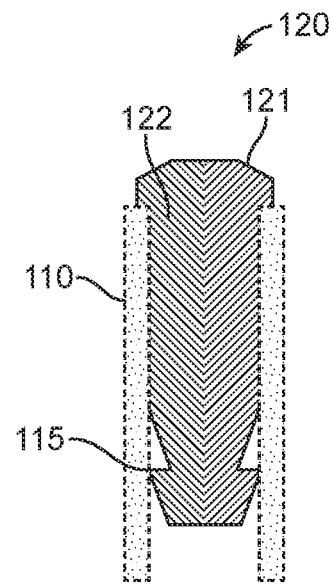
Figure 5C:
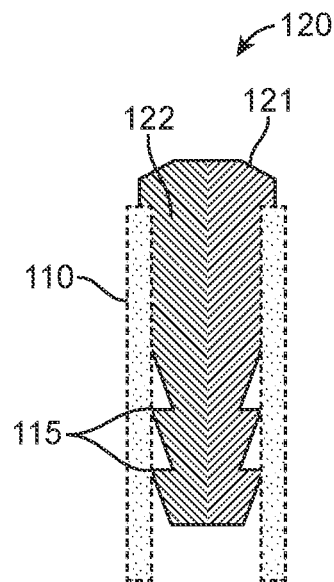
Figure 5D:
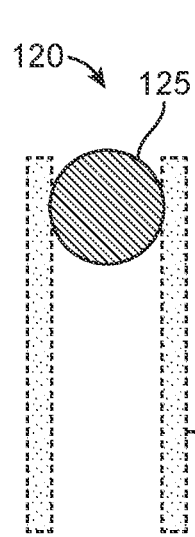
Figure 5E:
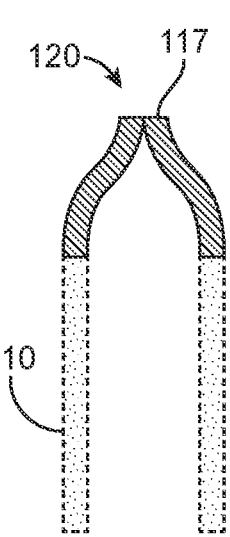
Figure 5F:
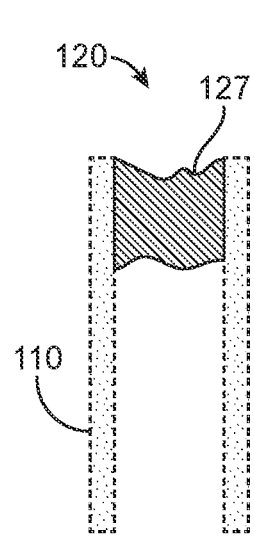
Figure 5G:
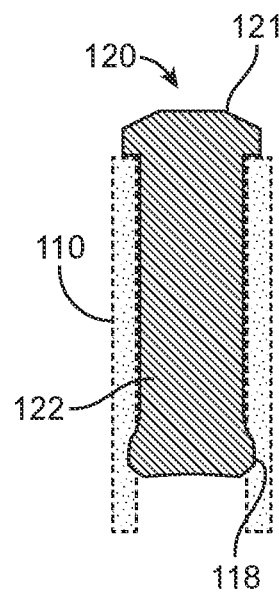

Each of the elements of the ASCA can take multiple forms that effect the same results. For example, as shown in FIG. 5A through 5G, plug 120 can have just one (FIG. 5B), instead of two (FIG. 5C), circumferential projections 115, or a plug shaft section 122 can be smooth sided (FIG. 5A). In other variations plug 120 can be a small ball bearing or spherical plug 125 (FIG. 5D) or the plug can be a measured amount of hardening material, for example, glue 127 injected into the end of the catheter 110 (FIG. 5F) or the distinct plug can be replaced by simply sealing the device end of catheter 110 (FIG. 5E). This seal can be created by pinching an open end 117 of the catheter and thermally sealing it closed, by gluing it closed, or by any other convenient means for eliminating a distinct plug component. In yet another variation, shown in FIG. 5G, plug 120 includes a shaft section 122 that is generally smooth sided except for a bulbous protrusion 118 at its tip.

In many variations plug 120 comprises plug shaft section 122 and a plug head 121. wherein plug shaft section 122 has a main diameter substantially equal to the internal diameter of catheter 110 while plug head 121 has a diameter larger than the internal diameter of catheter 110 to facilitate insertion and/or removal of plug 120 from the catheter and, in some variations, plug head 121 has a diameter larger than the external diameter of catheter 110 to improve retention of the catheter valve section 110C inside balloon jacket 210 as the major portion of the catheter is removed from the patient's body. In some variations the plug shaft section 122 comprises one or more projections 115 or teeth, wherein the teeth are disposed to permit plug 120 to be inserted into catheter valve section 110C with relatively little extra resistance but are shaped to dig into the relatively soft catheter material when force is exerted in the direction to extract plug 120 from catheter 110. Furthermore, for reasons discussed below and shown in FIG. 2B, the diameter of the teeth may be, by design, selected to form localized expanded bands, rings, or bulges 116 around the exterior of catheter 110. The region having these expanded bands is the interference region, so-called because the region has a mechanical interference with the engagement elements in jacket 210.

Plug 120 may be fabricated from any substantially incompressible, bio-compatible material. In one variation the plug is fabricated from stainless steel while in other variations the plug is fabricated from a polymer. In one variation in which a ball bearing is used as plug 120, the diameter of the ball bearing is designed to provide substantially the same functions as a toothed plug, that is, the diameter of the ball bearing is slightly larger than the internal diameter of the catheter, thus both plugging catheter 110 and forming one expanded band around the exterior of catheter 110.

Figure 6A:
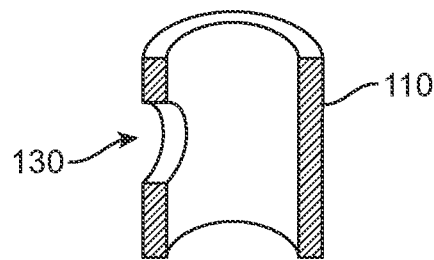
FIGS. 6A-6C illustrate variations of fill ports for an ASCA.
Figure 6B:
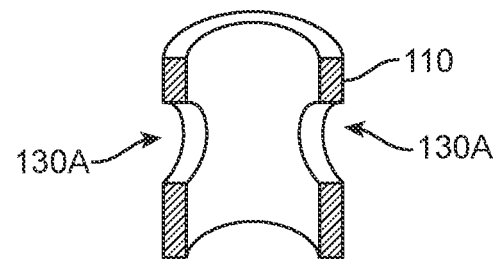
Figure 6C:
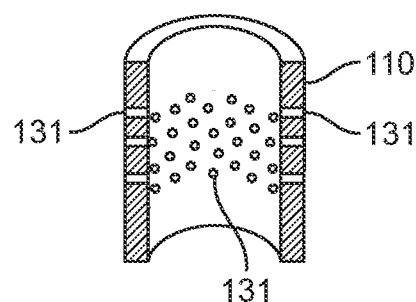

Similarly, as shown in FIG. 6A through 6C, fill port 130 illustrated in FIG. 2A can be functionally replaced by other designs. FIG. 6A illustrates a single fill port 130 in catheter 110, whose size is determined by the net port open area designed to fill the balloon without creating excessive backpressure or slow fill rates. In FIG. 6B the single fill port replaced by two or more, possibly smaller, ports 130A. These two ports are shown as diametrically opposed but they may be located anywhere around catheter 110. Further, port 130 can even be replaced by micro-drilled perforations 131, as shown in FIG. 6C, in a band around the catheter 110, this latter approach maintains rotational symmetry of the structure of the catheter 110 while still providing the desired net open area in the catheter. Laser micro machining by a vendor such as Resonetics, 44 Simon St. Nashua, NH can be advantageously used to create these micro-drilled perforations 131 in the catheter material.

Figure 7A:
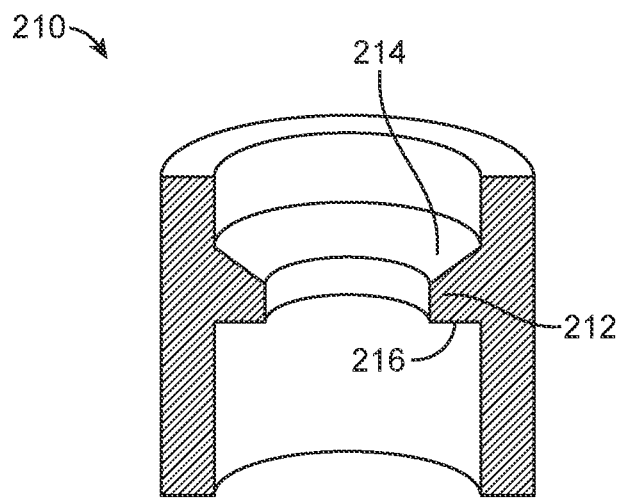
FIGS. 7A-7C illustrate variations of a catheter jacket for an ASCA.
Figure 7B:
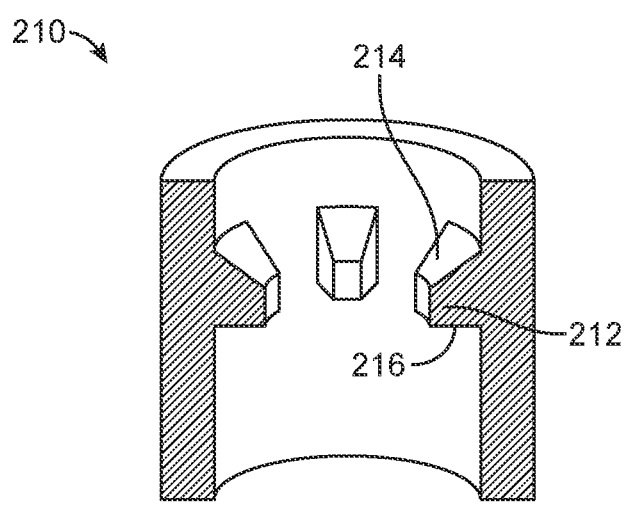
Figure 7C:
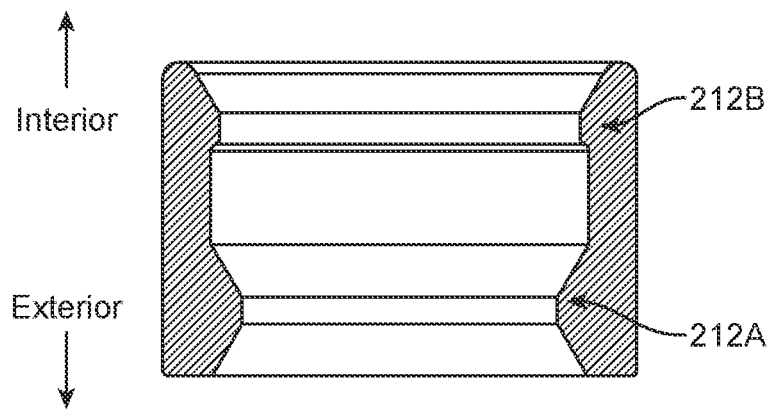

FIGS. 7A-C illustrates in sectional views variations of catheter jacket 210. In its most basic configuration, not illustrated, jacket 210 comprises a rigid cylindrical tube. In some variations jacket 210 has an internal diameter smaller than the catheter's outer diameter by a small amount, say 0.010 inches. In many variations, jacket 210 further comprises one or more raised engagement elements 212, wherein the elements 212 may be distinct bumps, knobs, or teeth, as shown in FIG. 7B, or they may be continuous ridges or rings as shown in FIG. 7A. In all cases engagement elements 212 reduce the internal clearance of the jacket to be less than catheter's 110 outer diameter to provide frictional engagement, or mechanical interference, between the jacket 210 and the interference region of catheter 110. In some cases, the engagement element can gently dig into the exterior of catheter 110. This diametrical difference is preferably between 0.001 inches and 0.050 inches; more preferably between 0.005 inches and 0.020 inches; and most preferably between 0.006 and 0.010 inches In some variations one or more of these raised elements may be asymmetric relative to the axis of symmetry of jacket 210, that is, the interior edge 214 and the exterior edge 216 may have different slope angles. In one variation the interior edge 214 is sloped to facilitate pulling catheter valve section 110C from the exterior side into jacket 210 to seal the ASCA while exterior edge 216 is more perpendicular to the interior wall of jacket 210 to inhibit, but not preventing, catheter valve section 110C from moving inwardly after the rest of catheter 110 has been torn away.

In other variations, as suggested in FIG. 4B, other engagement elements 212 may be configured to help form a fluid tight seal when plug 120 is pulled into jacket 210. In some variations, as shown in FIG. 7C, there may be two or more sets of engagement elements. The outermost (that is, closest to the exterior of device 100) engagement elements 212A have a small enough inner diameter to prevent plug 120 (shown as ball bearing 125 in FIG. 4B) from being pulled out jacket 210 when catheter 110 is extracted, whilst innermost elements 212B prevent plug 120 from migrating back into balloon reservoir 104 once the plug is in the sealing position. Innermost elements 212B also help to form a fluid-tight seal by squeezing spherical plug 125 against outermost elements 212A when there is a compressible section of catheter therebetween.

Some of engagement elements 212 can be configured to compress and dig into catheter 110 to hold catheter valve section 110C inside device 100 under small, incidental extractive loads but not retain catheter valve section 110C inside the device under the larger, intentional extraction load used to detach the catheter from the device. As illustrated in the graph in FIG. 7D, the frictional force holding a prototypical polymeric catheter back from extraction generated by outermost or exterior engagement elements 212A of a compatibly designed jacket may be determined at the time of design to span a wide range.

Some variations of ASCA 10, as illustrated in FIG. 3C, incorporate a single, plug-port member 128, in which various the features located in the catheter valve section 110C can be integrated together. The integrated features can include plug 120, which stops the filling fluid from exiting the fluid path when ASCA 10 is in the closed configuration, fill ports 130, which comprise one or more lumens to allow fluid to fill device 100, and the weakened section 151, which defines the location at which the catheter 110 will disconnect from the ASCA.

Figure 7D:
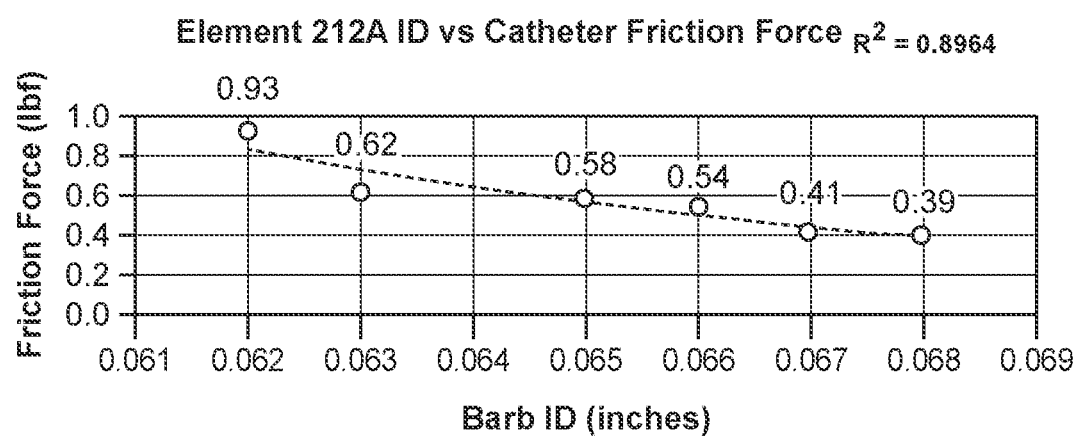
FIG. 7D illustrates the relationship between the interior diameter of the exterior engagement element of FIG. 7C and the frictional force holding a catheter in place.
Figure 7E:
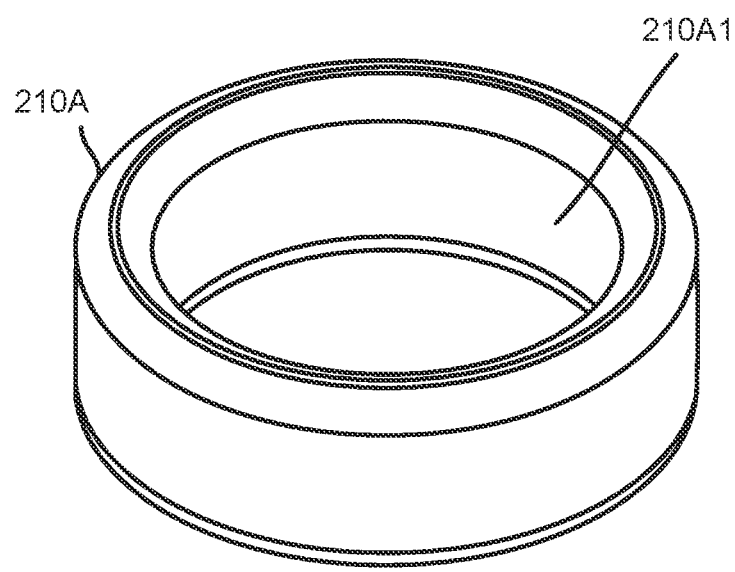
FIG. 7E illustrates an isometric view of a sealing ring.

FIG. 7E illustrates an isometric view of sealing ring 210A, which can be used in place of catheter jacket 210 in ASCA variations using a plug-port member. The interior surface 210A1 of sealing ring 210A can be smooth and tightly dimensioned to match the exterior surface of plug-port member 128.

Figure 7F:
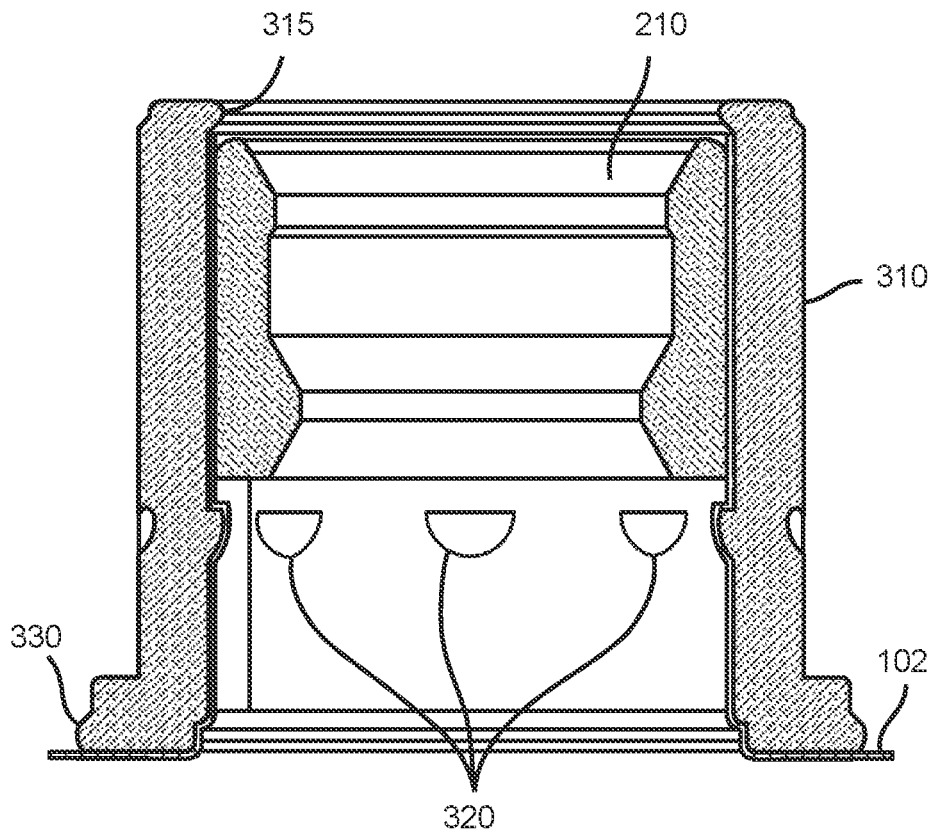
FIGS. 7F-7G are cross-sectional views of installed variations of a wall anchor.

As shown in cutaway FIG. 7F, in some variations jacket 210 may be held in place by a balloon wall anchor 310. In variations utilizing a balloon wall anchor, the thin film of material (either in the form of a section of the balloon wall 102 or a separate patch of material) can be pinched between catheter jacket 210 and balloon wall anchor 310, locking catheter jacket 210 in place in the balloon wall. As shown in FIG. 7F, anchor 310 may comprise one or more internal rings or teeth 320 to lock jacket 210 in place. Teeth 320 can be shaped to allow jacket 210 to slide over the teeth when being inserted from the exterior side of the device 100 but which lock the jacket 210 in place once the end of the jacket 210 passes the edge of the teeth 320.

Anchor 310 can also comprise an inward-facing lip 315 which can prevent catheter jacket 210 from entering the interior of the balloon device. Some variations of anchor 310 can comprise a flared exterior facing end 330, as shown in FIGS. 2B and 3A. Flaring this end of wall anchor 310 can provide a smooth and expanded contact surface between the anchor and the thin-film wall material, reducing the probability of tearing the wall material. In some variations anchor 310 can be fabricated from polymer material to reduce the probability of damage to the thin film wall 102 material, which can be sandwiched between jacket 210 and anchor 310. Wall anchor 310 can be attached to the wall by pinching wall material between the catheter jacket 210/ scaling ring 210A and the anchor or by glue, welding or other attachment means. The wall anchor 310 can be located interior, exterior, or partially exterior to the wall 102 of device 100.

Figure 7G:
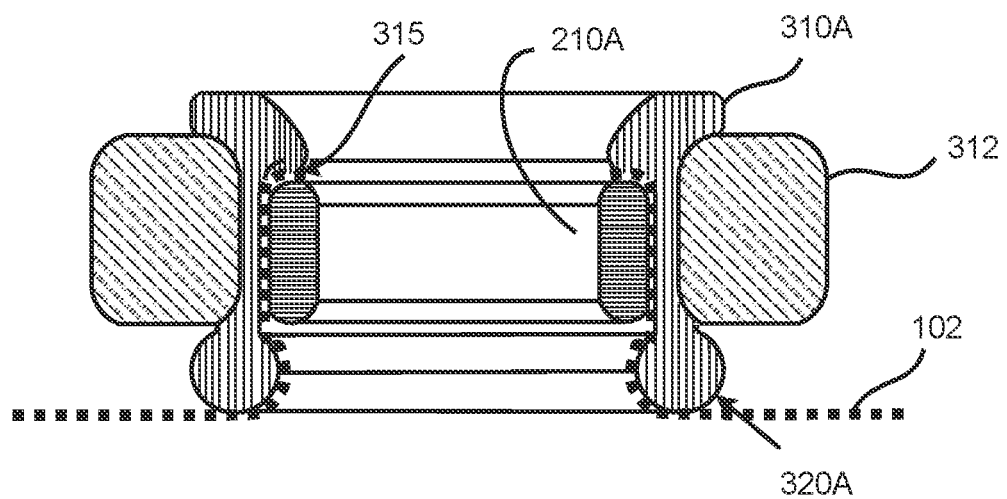

FIG. 7G shows another variation of the wall anchor 310A having inward facing lip 315 and a molded ring 320A. Ring 320A can be rounded to provide a smooth transition to protect wall 102 as it changes direction and can provide a captivation feature within the interior passage of wall anchor 310A to help maintain sealing ring 210A in wall anchor 310A. A radiopaque marker 312 can be provided adjacent to the wall anchor 310A to aid locating device 100 during deployment. In this variation, wall 102 wraps around the inside of the ring 320A and is pinched or captivated between anchor 310A and sealing ring 210A. The portion of wall 102 stretched across a top portion of sealing ring 210A during captivation is removed after captivation to restore fluid path 112 through wall anchor 310A and sealing ring 210A.

Figure 8A:
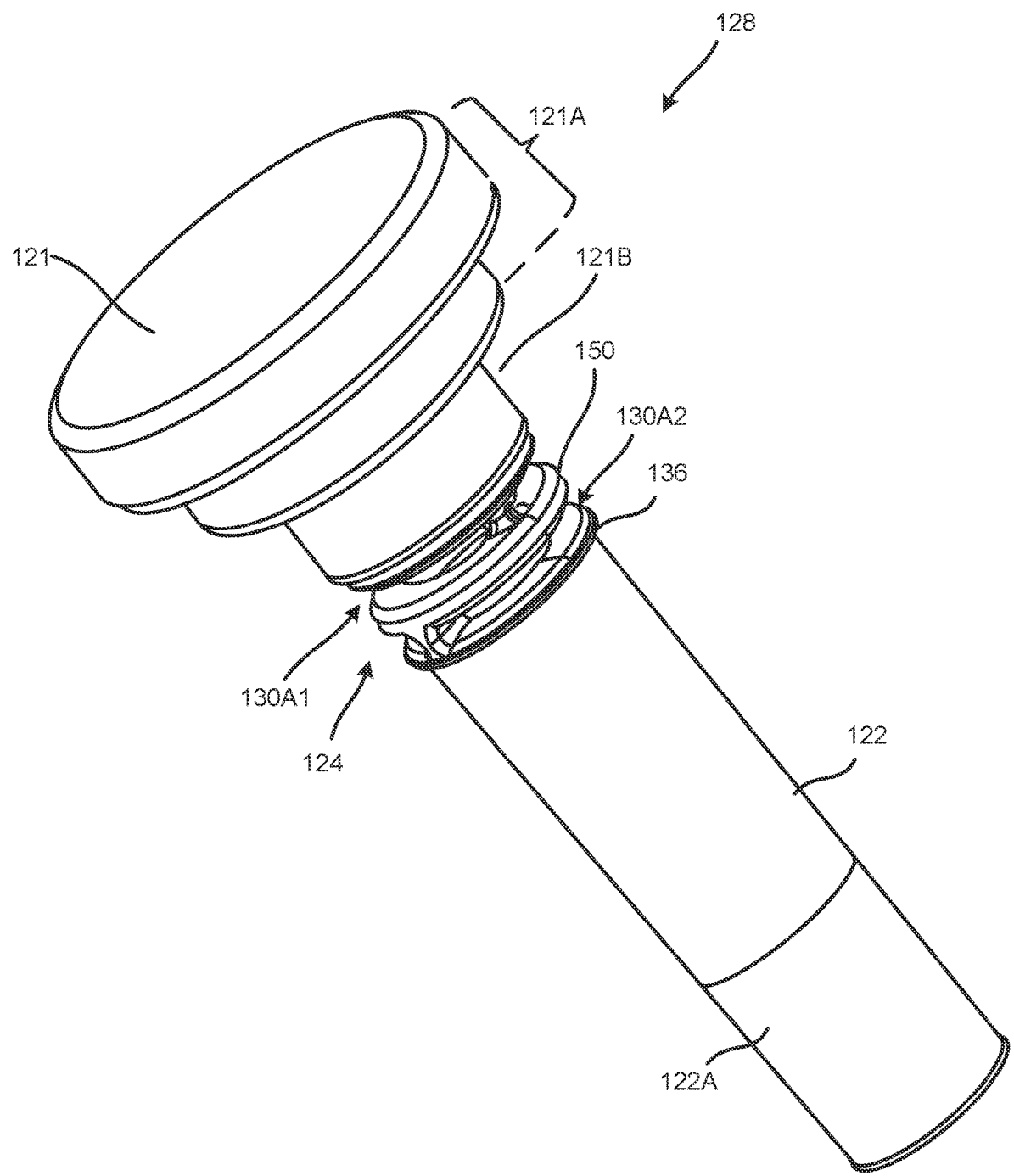
FIG. 8A is an isometric view of a variation of a plug-port member for an ASCA.
Figure 8B:
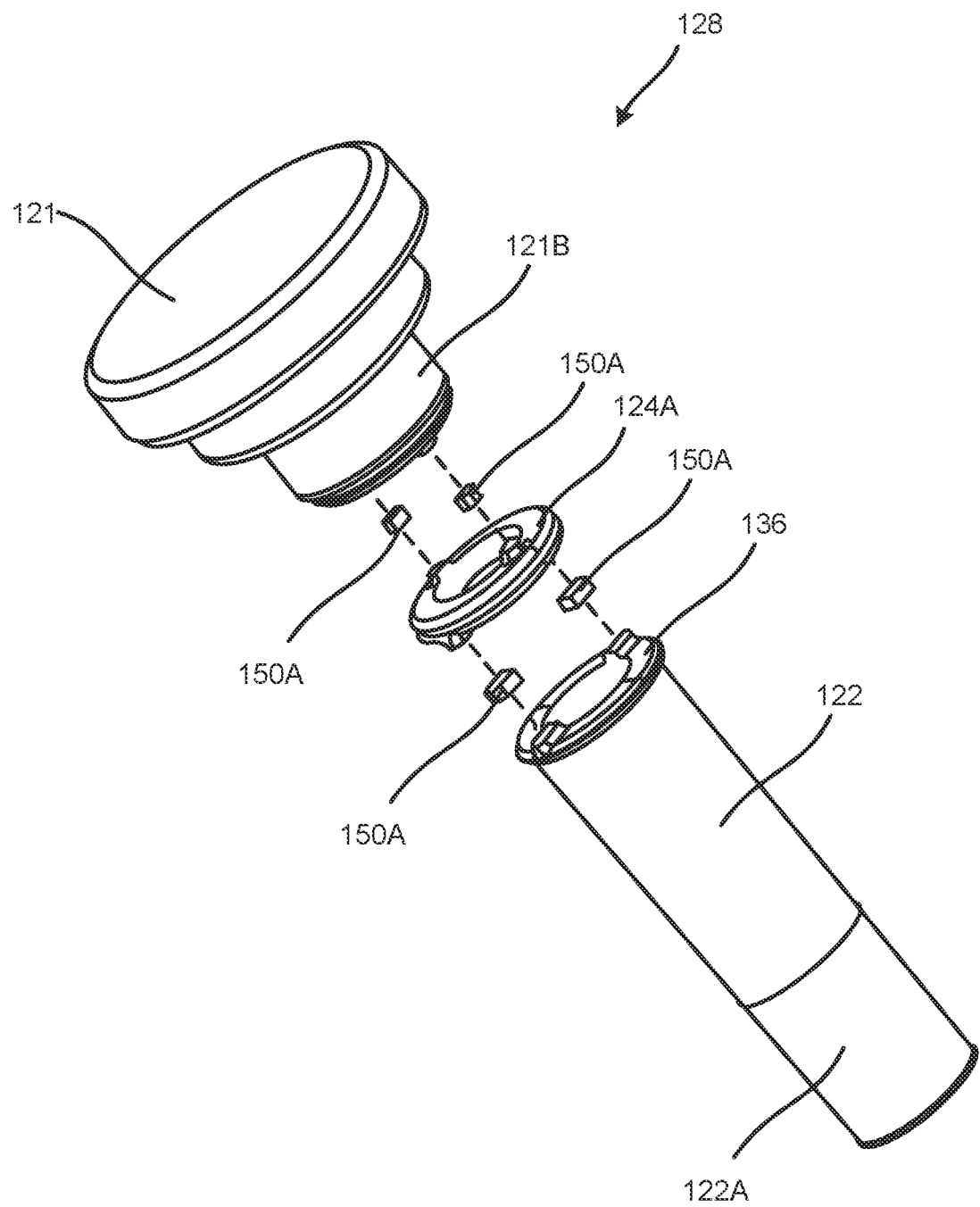
FIG. 8B is an exploded view of the plug-port member of FIG. 8A.

As illustrated in FIG. 8A and FIG. 8B, one variation of plug-port member 128 can be an integrated or monolithic element that comprises plug 120, fill ports 130, and weakened section 151. FIG. 8A is an isometric view of plug-port member 128 and FIG. 8B is a pseudo-exploded, isometric view of a one-piece plug-port member 128 of FIG. 8A. Plug-port member 128 can be injection-molded from a thermoplastic polyurethane or other thermoplastic suitable for injection molding. As shown in FIG. 8A, plug-port member 128 can comprise a plug section 121 comprising head cap 121A and head body 121B, wherein head body 121B has a smaller diameter than head cap 121A. The diameter of head body 121B can be designed to be an interference fit with anchor 310A, illustrated previously in FIG. 3C, while the larger diameter of head cap 121A acts as a stop to prevent the entirety of head 121 from entering anchor 310A.

As further illustrated in FIG. 8A, this variation of integrated plug-port member 128 can comprise plug shaft section 122. Shaft section 122 can have a diameter slightly larger than the interior diameter of catheter 110 such that shaft section 122 can be fully and tightly inserted into catheter 110 by stretching the catheter diameter. The diameter of shaft section 122 can be based on the material properties of plug-port member 128 and catheter 110; the insertion force required to insert plug-port member 128 into catheter 110; and the retaining force needed to prevent slippage as catheter 110 is withdrawn from the ASCA. In some variations, shaft section 122 can comprise a tapered tip region 122A where the tip end of the taper has an outer diameter slightly smaller than the inner diameter of catheter 110 to allow an easier insertion of shaft section 122 into catheter 110.

Plug-port member 128 can further comprise a port section 124. In some variations port section 124 can comprise a lip 136 having a diameter slightly larger than shaft section 122. Lip 136 can act as a stop to prevent plug-port member 128 from accidentally being inserted too far into catheter 110, which might reduce or stop the flow through the fill ports 130.

In this variation, port section 124 can include both the fill ports and the weakened section 151. In previously described ASCA variations, the one or more fill ports 130 and the weakened section 151 can be formed by removing material from catheter 110, for example, in FIG. 2A.

The plug-port member 128 can comprise a higher elastic modulus than an elastic modulus of the catheter 110. Accordingly, as part of the valve closure process described below, the catheter 110 can stretch during application of a pulling force towards the fill end and prior to the pulling force exceeding a frictional resistance force of the device 100. After the frictional resistance force is exceeded, plug-port member 128 is seated into the anchor 310 via a stored energy from the stretching of catheter 110. The catheter 110 can also be inelastic to achieve seating the plug-port member 128 into the anchor 310.

FIG. 8B is an exploded view which separates sections of the plug-port member 128, which can be made from a single part or from individual components. In the illustrated variation, port section 124 can comprise two axial layers 130A1, 130A2, each comprising two fill ports, leaving only small connectors 150A. Layer 130A1 and layer 130A2 can be defined by a thin, separating layer, annular disk 124A. Annular disk 124A can thus be attached on one side to head 121 and on the other side to shaft section 122 by the one or more connectors 150A. The one or more small connectors 150A have significantly lower tensile strength than the adjacent full circumference head body 121B, annular disk 124A, or shaft section 122 and function as weakened section 151, Other variations of plug-port member 128 can comprise a single axial layer comprising one or more fill ports 130 or more axial layers and one or more fill ports 130 per layer.

Figure 8C:
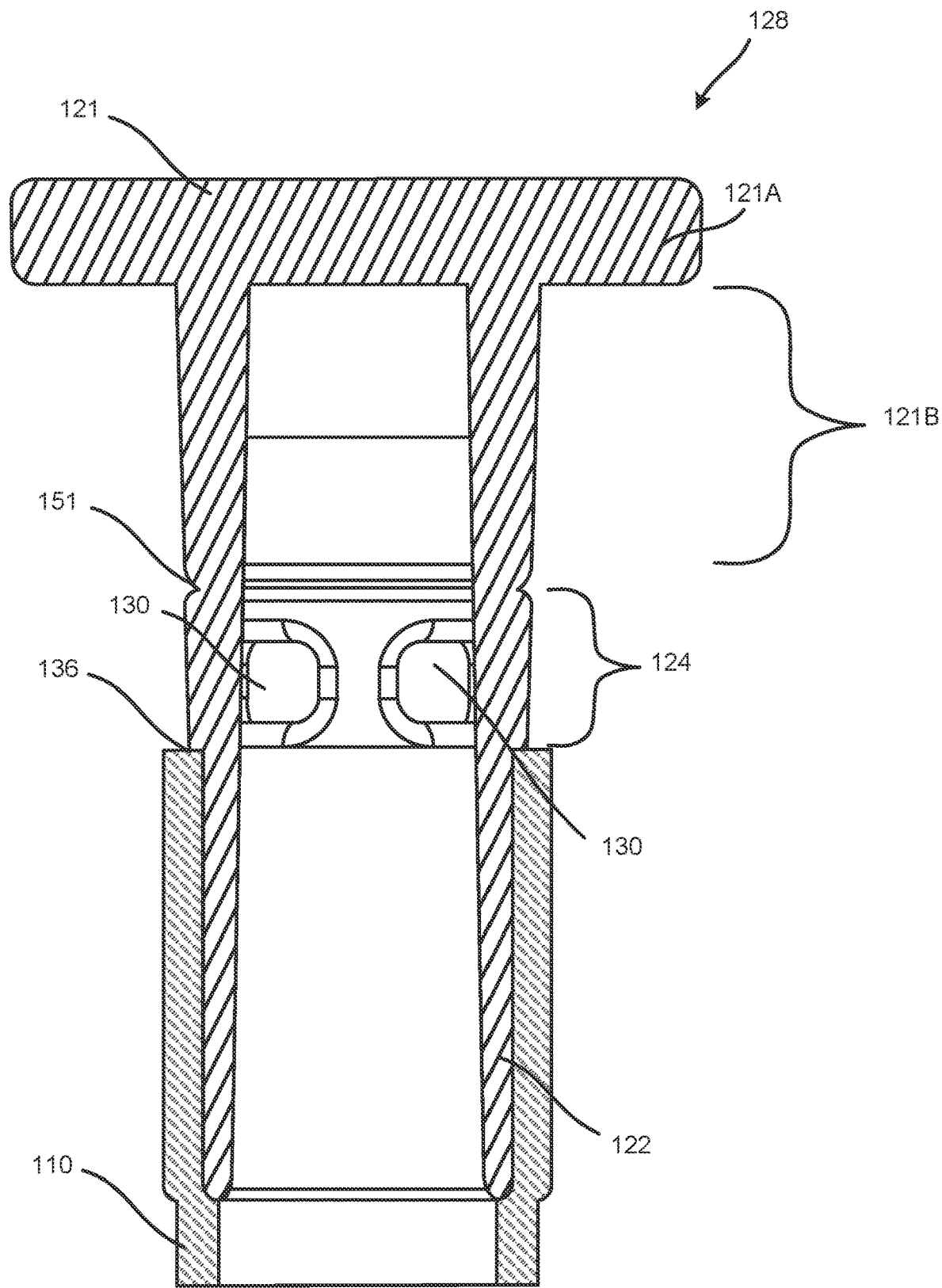
FIG. 8C is a sectional view of another variation of a plug-port member.

Another variation of an integrated plug-port member 128 is illustrated in cross-section FIG. 8C. This variation of plug-port member 128 can also comprise sections made from a single part. One section is the plug shaft section 122 which can have a diameter slightly larger than the interior diameter of catheter 110, where the exact diameter is based on the material properties of plug-port member 128 and catheter 110; the insertion force required to insert plug-port member 128 into catheter 110; and the retaining force needed to prevent slippage as catheter 110 is withdrawn from the ASCA. In some variations, shaft section 122 can also comprise a tapered tip region such that shaft section 122 can be fully inserted into catheter 110.

Still referring to FIG. 8C, another section of plug-port member 128 can comprise a port section 124. In some variations, port section 124 can be made distinct from plug shaft section 122 by a lip 136 having a diameter slightly larger than shaft section 122. Lip 136 can act as a stop to prevent shaft section 122 from being inserted so far into catheter 110 that all or some of the open area of fill ports 130 is obstructed, which can reduce or stop the flow through the fill ports. The outer diameter of port section 124 can be less than the inner diameter of anchor 310A (not shown) to prevent the port section 124 from binding when it is pulled into anchor 310A after device 100 is filled. In this variation, port section 124 can include one or more fill ports 130. The number and size of the fill ports can be engineered to provide a desired fill rate and can be distributed uniformly around the circumference of port section 124.

Still referring to FIG. 8C, another section of plug-port member 128 can comprise head 121. Head 121 can further comprise head cap 121A and head body 121B, wherein head body 121B has a smaller diameter than head cap 121A. The diameter of head body 121B can be designed to be an interference fit with anchor 310A, while the larger diameter of head cap 121A acts as a stop to prevent the whole head 121 from entering anchor 310A. Head body 121B can perform the plugging function of catheter valve section 110C.

Head 121 can be distinguished from port section 124 by weakened section 151, which in this variation can be a molded circumferential groove that reduces the wall thickness, and therefore the tensile strength at the weakened section 151 location. As indicated in FIG. 8C, this plug-port member 128 can decouple the engineering of weakened section 151 from the engineering of port section 124.

Figure 8D:
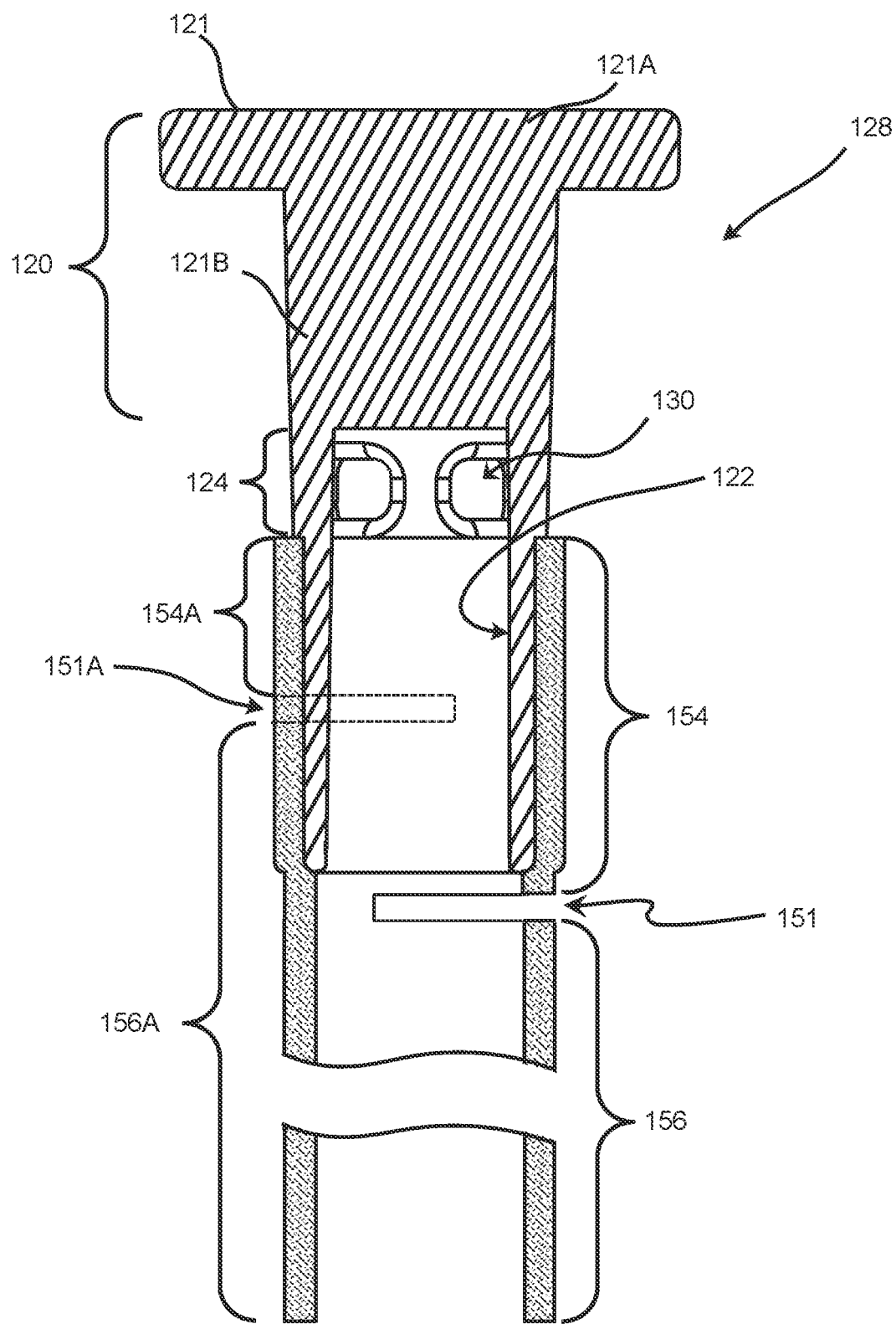
FIG. 8D is a sectional view of yet another variation of a plug-port member.

As illustrated in FIG. 8D, a variation of plug-port member 128 and catheter 110 can have a weakened section 151 located on catheter 110. The weakened section 151 can be between a residual section 154 and a removable section 156 of catheter 110. The residual section 154 can be disposed fully detached or partially attached to the shaft section 122 prior to catheter disengagement. In general, the elements that comprise the ASCA are intended to control the frictional force/retention force that holds the catheter 110 in the ASCA during a fluid-fillable balloon device 100 deployment process while allowing the catheter 110 to be disengaged from the device after it is filled.

Alternatively, a weakened section can be located on catheter 110 further towards the device end 110A (see alternative element 151A), for example, at a location where the catheter 110 overlaps shaft section 122 of plug-port member 128. In this variation, the alternative removable section 156A can be lengthened and the alternative residual section 154A can be shortened.

Figure 8E:
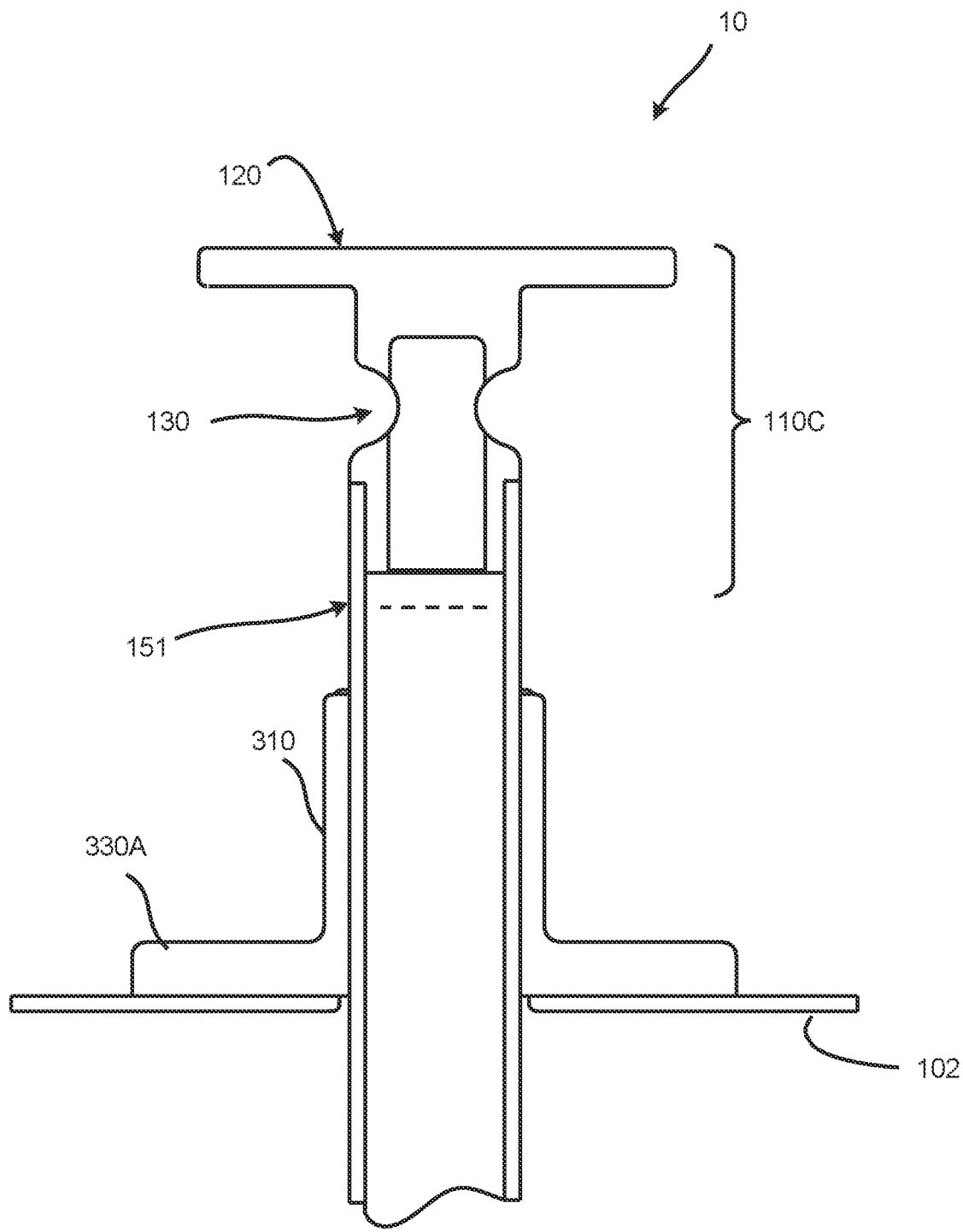
FIG. 8E is a sectional view of yet another variation of a plug-port member.

FIG. 8E is a conceptual illustration of yet another variation of ASCA 10. In this variation, plug-port member 128 comprises plug 120 and ports 130 and catheter 110 comprises weakened section 151. In this variation, wall anchor 310 can be configured as a cylindrical tube with an exterior facing end in the form of an annular disk 330A instead of the flared exterior facing end 330 of the variation of FIG. 2B. Further, in this variation wall anchor 310 does not include a sealing ring. In the illustrated variation, wall anchor 310 is attached directly to device wall 102, instead of pinching wall 102 between the interior wall of anchor 310 and the exterior wall of a sealing ring. Typically disk 330A is attached to wall 102 by gluing or welding, where the extended contact area between the disk and the wall creates a stronger bond than can be achieved with the limited contact area between the wall and flared exterior facing end 330. Lacking a sealing ring, the interior diameter of wall anchor 310 is sized to be an interference fit for the outer diameter of catheter valve section 110C.

Figure 9A:
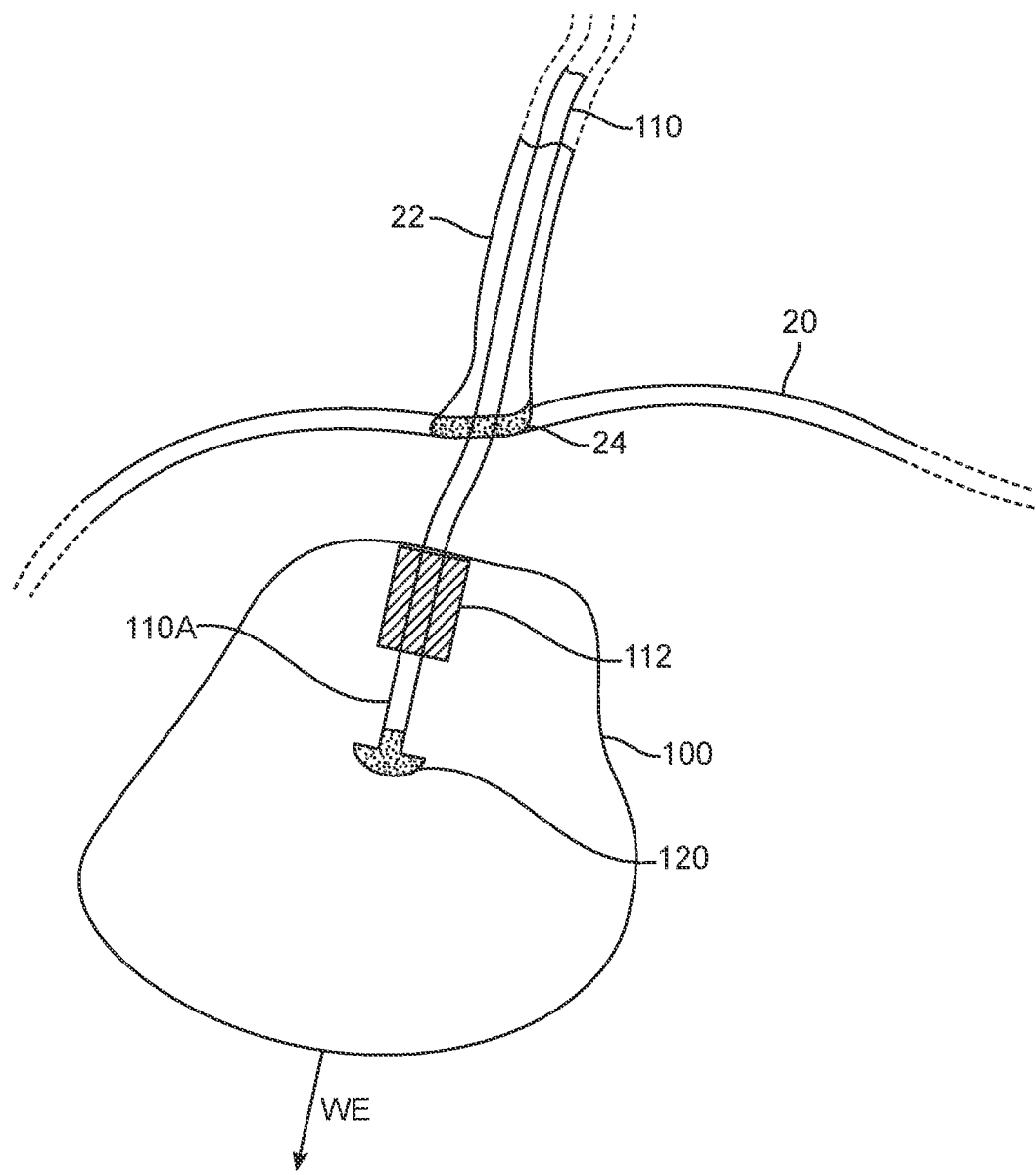
FIG. 9A is an illustration of an ASCA before sealing.
Figure 9B:
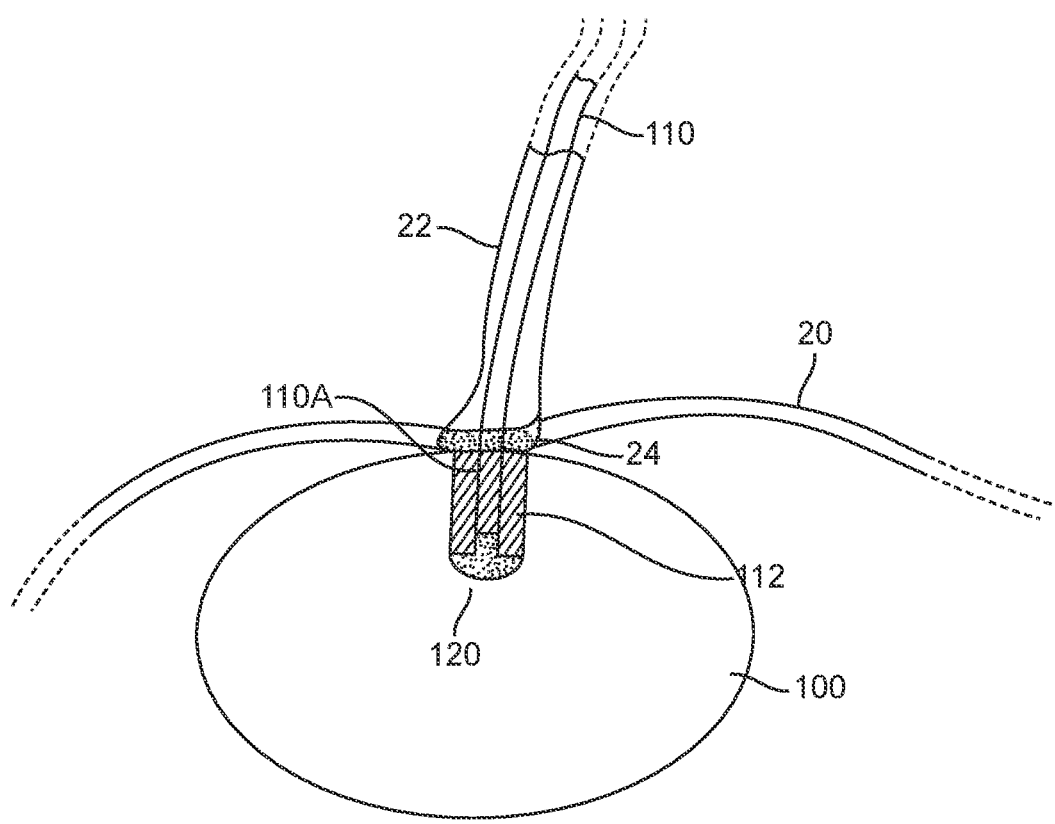
FIG. 9B is an illustration of an ASCA in the sealed condition.
Figure 9C:
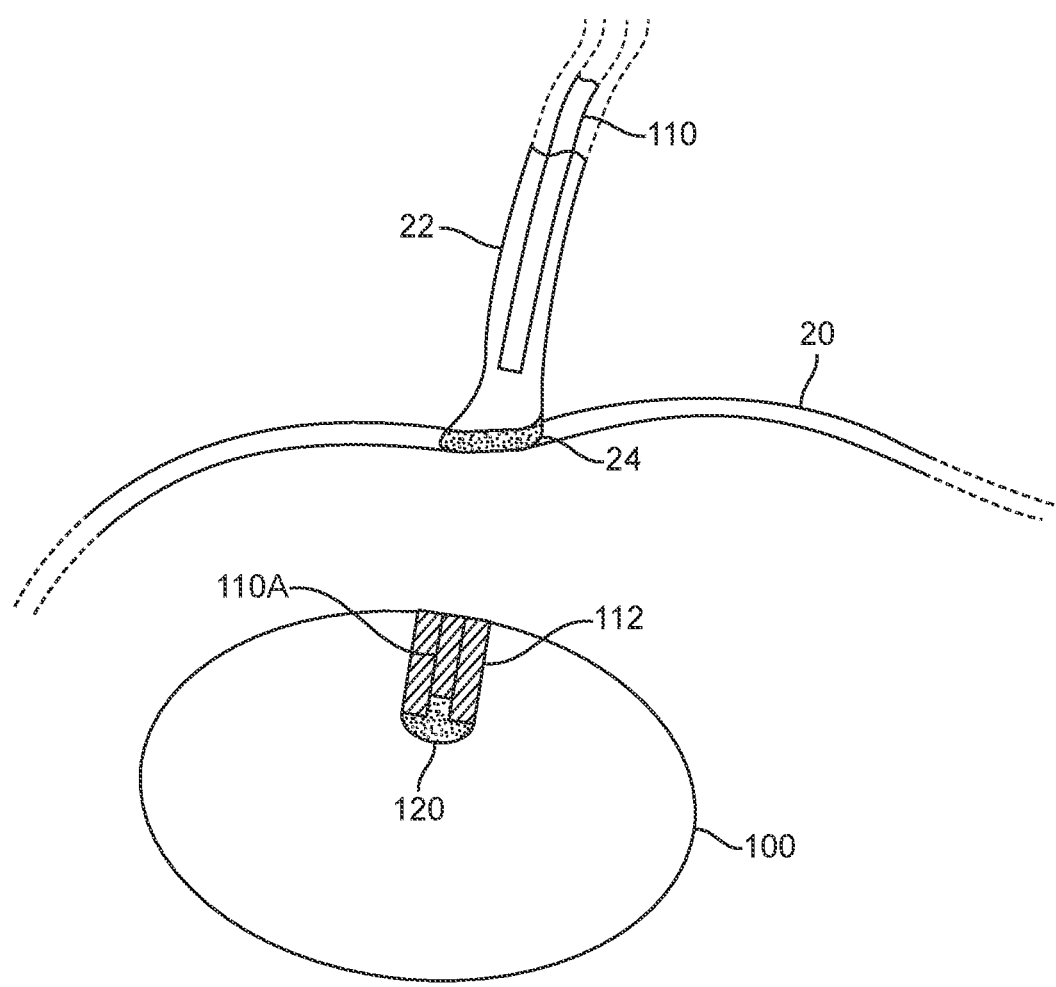
FIG. 9C is an illustration of an ASCA after release of the device.

As illustrated in FIGS. 9A-9C, there are three stages in the deployment process, where the maximum retaining force that holds the catheter within the device varies in each stage.

As shown in FIG. 9A, for a balloon variation, the first stage that occurs after positioning the device in the stomach 20 is a filling stage, during which the medical caregiver begins to infuse fluid into the empty, or partially empty, device 100. During this stage, device 100 can be considered as a weighted mass at the end of the catheter 110. As device 100 fills with fluid, especially when the fluid is a liquid, the weight at the end of the catheter increases from the weight of the un-inflated thin film device 100, typically a few grams, to the weight of the enclosed volume of fluid. In one variation, the filled balloon weight ("WB") is approximately 500 grams. In some variations, the filled device is at least partly supported by surrounding tissue or, in the case of a gastric balloon, by the contents of the stomach, which reduces the effective weight ("WE") applied by the balloon on the catheter. To keep device 100 from pulling away from, or sliding off, catheter 110 before the filling process is completed, the retention force ("FR") or sliding resistance threshold force that retains the catheter within the valve must be greater than the effective weight to prevent premature detachment of the catheter or sealing of the valve. While stomach wall 20 is shown in FIG. 9A, it should be understood that the device can be used similarly in other manually inaccessible cavities.

As shown in FIG. 9B, a second stage of the deployment process seals the ASCA. Closing this valve requires pulling valve section 110C of catheter 110 into fluid path 112 such that the fill port 130 is withdrawn from the reservoir of the device 100. As illustrated, this stage of the process comprises pulling the catheter 110 towards the fill end (e.g., towards the esophagus 22) until filled device 100 encounters resistance to motion against the esophageal sphincter 24. Once device 100 abuts sphincter 24, continued application of the force increases the tension in catheter 100 until the tension is greater than, and overcomes, the FR, allowing the catheter valve section 110C to slide into fluid path 112 with a sliding resistance somewhat below the sliding resistance threshold. This movement closes the valve. The force required to overcome FR is called a "closing force" or "FC". In general, the FC is a "threshold" force, meaning that once FC overcomes FR, the force required to maintain movement of the catheter will be less than FC, since sliding friction is less than static friction/resistance.

In some variations, as catheter 110 is pulled into fluid path 112, plug 120 reaches engagement elements 212A (not shown in FIGS. 9A-9C) and cannot move any further. In the illustrated variation, plug 120 is prevented from entering too far into fluid path 112 by plug head 121.

The third stage of deployment is illustrated in FIG. 9C, where the majority of catheter 110 is disconnected from device 100 and is removed from the patient's body. Only valve section 110C, which is part of ASCA 10, remains in device 100 after device deployment. With the device lodged against esophageal sphincter 24 the disconnection of catheter 110 is effected by pulling on the catheter with increasing force until the tension in catheter 110 exceeds a tear force, FT, which causes the catheter to separate at weakened section 151, where weakened section 151 can be designed to keep the tear force FT below an esophageal force ("FE") that would damage the esophageal sphincter. Note that in some variations the weakened section 151 is a tear slit while other variations use other means of forming a weakened section to create the desired tear location to achieve a safe disconnection of catheter 110.

The primary means of controlling the various forces are the material properties of the sliding component and the fixed components and the internal diameters and profiles of the internal features of catheter jacket 210. For example, FIG. 7D illustrates the relationship between the internal diameter of an engagement element (Barb ID) and the frictional force/resistance felt by a catheter, as measured for an exemplary embodiment of engagement elements 212A and catheter 110.

$FR>WE$ $FC>FR$ $FT<FE$ $FR<FE$ $FT>FC$ During the design of ASCA 10, several relationships must be considered. First, to prevent the catheter from moving during the balloon fill stage of deployment, $FR>WE$ $FC>FR$ $FT<FE$ $FR<FE$ $FT>FC$ $FR>WE$ $FC>FR$ $FT<FE$ $FR<FE$ $FT>FC$ Second, to initiate the closing of the ASCA by starting the catheter moving into the catheter jacket, $FR>WE$ $FC>FR$ $FT<FE$ $FR<FE$ $FT>FC$ $FR>WE$ $FC>FR$ $FT<FE$ $FR<FE$ $FT>FC$ Third, to prevent injury to the patient, $FR>WE$ $FC>FR$ $FT<FE$ $FR<FE$ $FT>FC$, and $FR>WE$ $FC>FR$ $FT<FE$ $FR<FE$ $FT>FC$ $FR>WE$ $FC>FR$ $FT<FE$ $FR<FE$ $FT>FC$ Finally, to prevent the weakened section from tearing before the valve is closed $FR>WE$ $FC>FR$ $FT<FE$ $FR<FE$ $FT>FC$ Based on experimental experience which determined both the WE and the FE, in one variation FR is preferably, 1.11 N<FR<7.12 N and more preferably 2.67 N<FR<4.89 N. Where 7.12 N was determined to be safely below FE for human patients. Further, 5.56 N<FT<7.12 N. Note that FC is not a free design parameter because it is always equal to the FR of the specific as—built valve (that is, the valve starts closing as soon as FC exceeds the threshold of FR).

The design of an ASCA with the various range of forces described above is especially useful in those situations where deployment, filling, sealing, and detachment of a device occurs remotely, for example, within the stomach. In such a case, it is desirable to close the valve and detach the conduit without supporting or holding the valve by supplementary means. Since the device is within the stomach, providing support to the valve or cutting the catheter would require a tool advanced through the esophagus causing the procedure to increase in complexity.

Figure 10A:
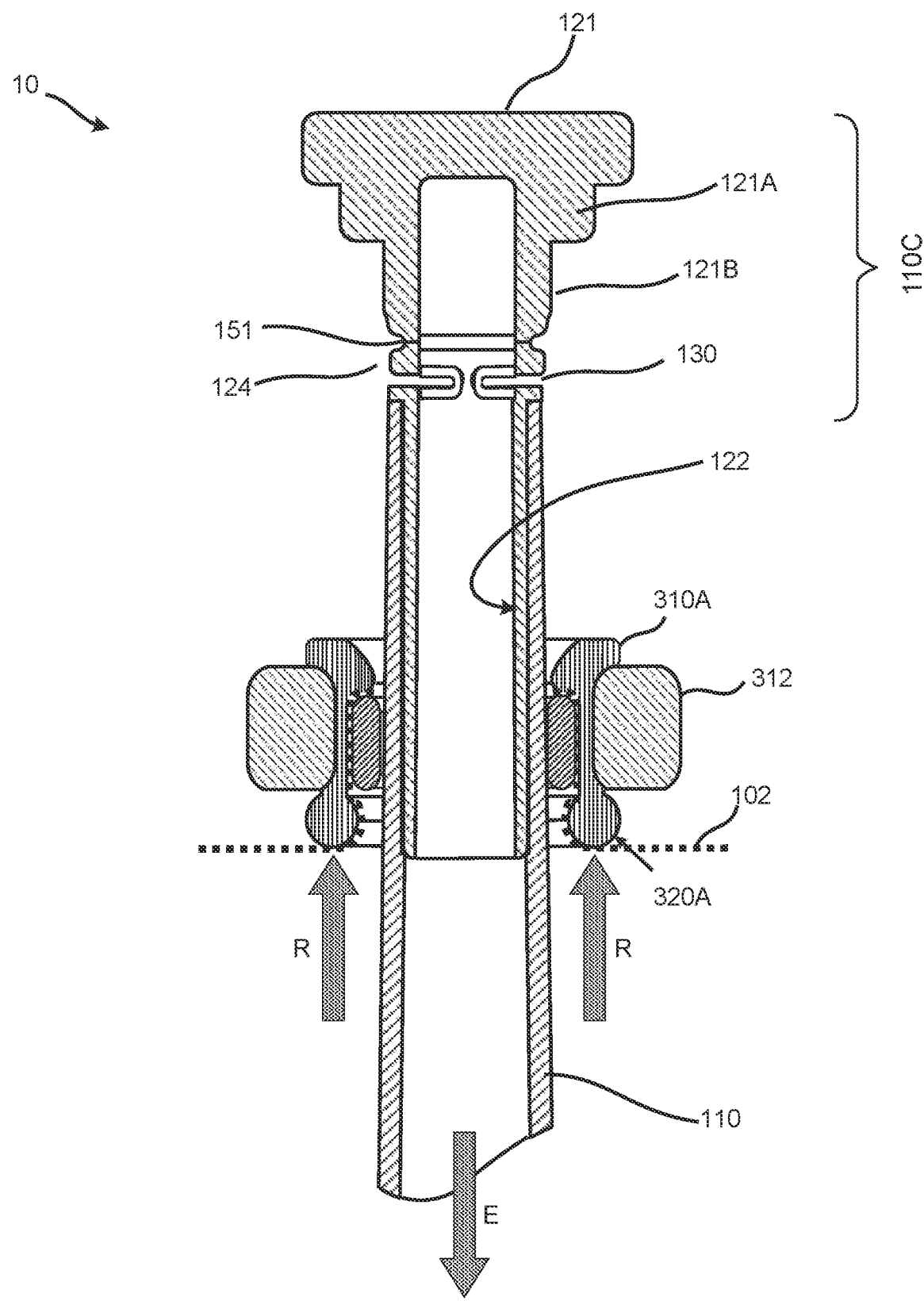
FIG. 10A is a sectional view of the variation of the ASCA of FIG. 3C before sealing.
Figure 10B:
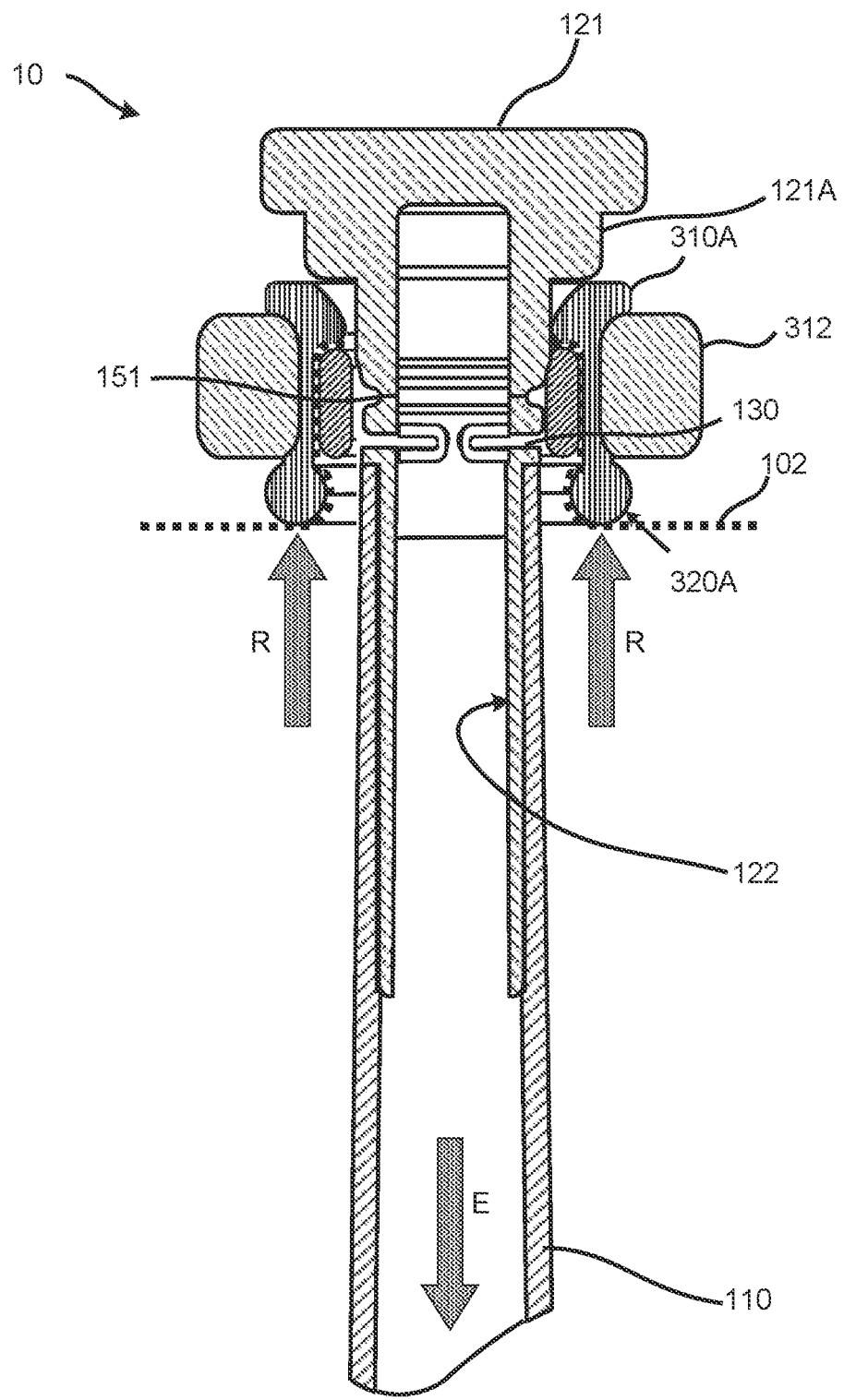
FIG. 10B is a sectional view of the ASCA of FIG. 3C in the sealed condition.
Figure 10C:
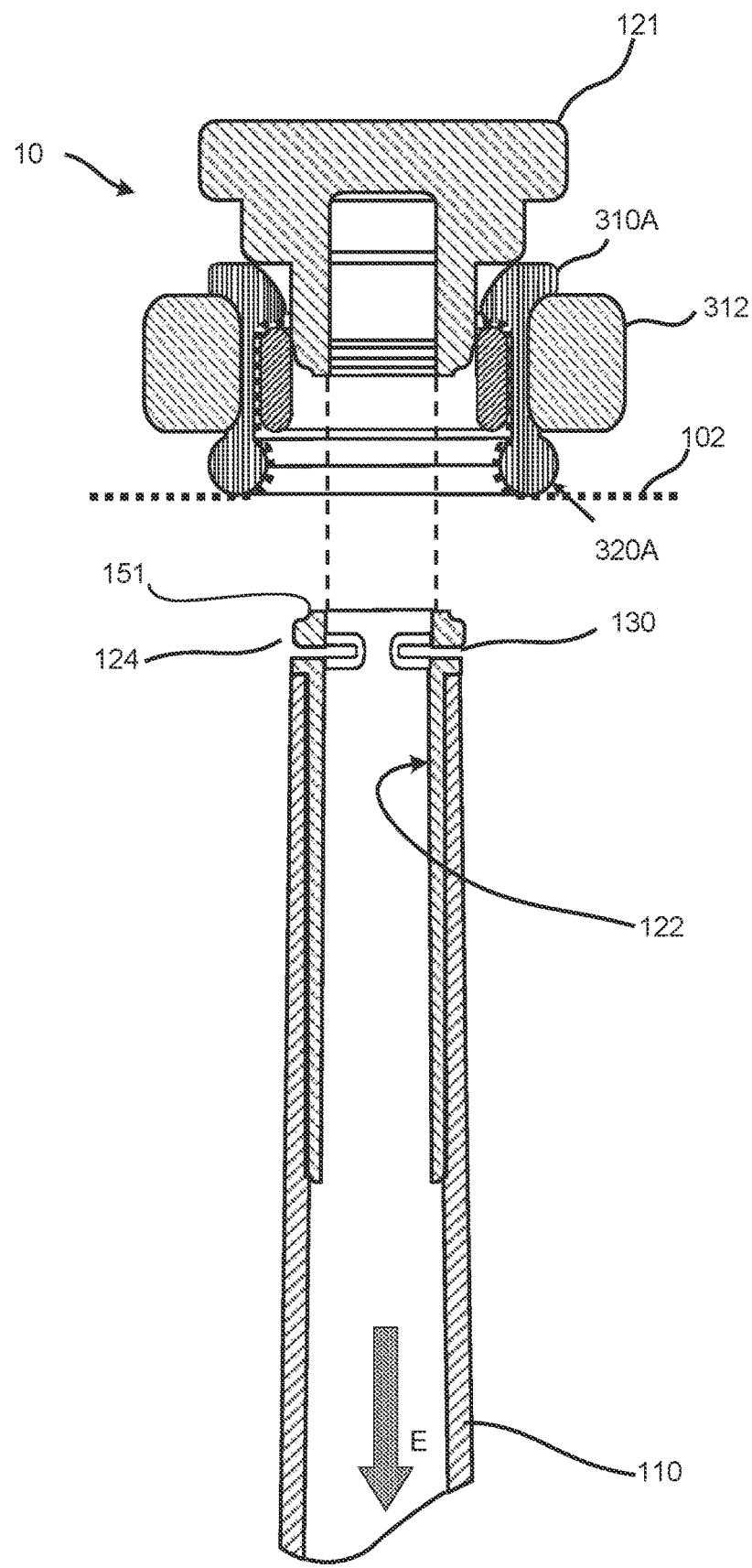
FIG. 10C is a sectional view of the ASCA of FIG. 3C after release of the device.

FIGS. 10A-10C illustrate the deployment process for an ASCA variation comprising a plug-port member. The first stage of device deployment is illustrated in FIG. 10A. The ASCA is installed in device 100 with anchor 310A attached to thin-film wall 102 by captivating wall 102 between sealing ring 210A and anchor 310A and device 100 has been placed in a remote cavity, typically the stomach. During device assembly, the catheter 110 is inserted through fluid path 112 such that valve section 110C is within the device reservoir 104 with ports 130 unobstructed by the sealing ring 210A or the wall anchor 310A. An optional radiopaque marker 312 can be positioned adjacent to the anchor 310 to aid locating device 100 during deployment. After deployment, the design-appropriate volume of filling fluid is introduced at catheter fill end and the device 100 is filled. Next, catheter 110 is withdrawn from the patient while leaving the device in-situ, which requires the catheter to disconnect from plug-port member 128.

At the stage of deployment in FIG. 10A, device 100 can be in the stomach and any encapsulating material has degraded or dissolved to release the balloon device. As shown, device 100 has been filled with fluid and is being pulled by extractive force, arrow E, up against a wall (not illustrated) of the remote cavity. Simultaneously, a resistive or reaction force, arrow R, is generated by the wall of the remote cavity, where the wall may be part of the anatomy of the patient (i.e., the pylorus or the esophageal sphincter), to resist and stop the motion of the device before sealing has begun.

FIGS. 10B and 10C illustrate the process of withdrawing catheter 110 from the patient, where the plug-port member 128 is pulled into the anchor 310A. FIG. 10B illustrates the catheter valve section 110C of FIG. 10A after it has been pulled through anchor 310A and scaling ring 210A and plug-port member head section 121 has been seated therein. At this stage, extractive force, arrow E, has yet to exceed the tear strength of weakened section 151. As described above, the diameter of head body 121B can be designed to be an interference fit with anchor 310A. In the illustrated variation, portions of sealing ring 210A are also an interference fit with head body 121B above the weakened section 151. As illustrated in corresponding FIG. 9B, the balloon can only reach this deployment stage when it abuts a wall 20 of the remote cavity in which it is deployed. In the gastric balloon example, the balloon abuts the esophageal sphincter, such that the wall provides the resistive or reaction force, arrow R. to hold the balloon from moving further when the catheter is being withdrawn from the patient.

FIG. 10C illustrates the final deployment stage, when catheter 110 has been disconnected from the device 100 and is free to be removed from the patient's body. As illustrated, head cap 121A and head body 121B are firmly seated and held in anchor 310A and scaling ring 210A while plug shaft section 122 and port section 124 have been disconnected at weakened section 151 by the continued application of outward extractive force, arrow E, towards the fill end, to weakened section 151. Extractive force E is generally applied to catheter 110 at or near catheter fill end 110B and transmitted by catheter 110 to ASCA 10. Extractive force E is increased until weakened section 151 breaks, disconnecting catheter 110 from ASCA 10, accelerating catheter 110 out of the body, and leaving device 100 free inside the remote cavity as a result. Once catheter 110 is disconnected, extractive force E is no longer applied to device 100 so the resistive or reaction force R disappears, having nothing against which to react.

The ASCA can be fabricated on a separate patch of balloon-compatible material or assembled in situ in a wall of the balloon device. A process for fabricating the automatic-scaling catheter assembly typically comprises the following steps:

1) Identifying a region of thin-film material balloon wall suitable for installation. Such region is typically substantially flat and approximately 45 millimeters in diameter for some variations. In some applications in which the balloon is a highly oblate spheroid this region may be at one of the poles of the spheroid. In other variations the installation region may be on a separate patch of material known to be compatible with the thin film material of the balloon. In typical variations the patch of material is between .0025 and .005 inches thick. The patch of material will later be installed over a hole in the balloon device in a region that is typically substantially flat, such as at one of the poles of a highly oblate spheroidal balloon. In certain variations the installation region may be on a seam in the balloon wall.
2) Placing the thin film material in a fixture comprising two rigid plates, each of which have a central through-hole with a diameter commensurate with the catheter jacket. The material region is sandwiched between the two plates and typically centered on the through hole.
3) Pushing the jacket up through the hole from a first side of the fixture, stretching the film over the jacket in the process. The first side of the fixture corresponds to the exterior of the balloon and defines an exterior side of the finished ASCA.
4) Pressing the wall anchor over the jacket and film from a second side of the fixture, captivating the film between the jacket and the wall anchor and removing the thin film blocking the lumen of the wall anchor/jacket subassembly. The second side of the fixture corresponds to the interior of the balloon.
5) Removing the jacket-film-anchor subassembly from the rigid plate assembly.
6) Optionally pressing the retaining ring or radiopaque marker over the subassembly from what had been the second side of the fixture. The retaining ring should be bottomed out against the end of the wall anchor.
7) Separately, preparing the catheter device end. This preparation depends on the ASCA variation but typically comprises:
    a. Creating one or more fill ports, if the port section is on the catheter.
    b. Cutting one or more tear-away slits or creating a weakened section if the weakened section is on the catheter.
8) Inserting the prepared catheter device end into the subassembly from the exterior side of the ASCA, allowing the device end to project past the end of the rest of the subassembly by a convenient working distance but at least far enough to expose the fill port(s).

9) Inserting the plug or the plug-port into the open lumen of the catheter device end or, alternatively, sealing the open lumen of the catheter device end.

10) Withdrawing the catheter from the exterior side of the ASCA to eliminate excess catheter length on the interior side of the ASCA, leaving the fill port(s) exposed.

The invention claimed is:

1. An implantable medical device comprising:
a device body having an internal reservoir and configured to expand in size upon delivery of a fluid into the internal reservoir;
an anchor structure affixed to a wall of the device body and having an interior passage;
a conduit having a fill end and a device end with a conduit lumen extending therethrough;
a plug-port member comprising a shaft section opposite to a plug section, with a port section located therebetween, wherein the shaft section comprises a shaft lumen in fluid communication with the port section, where the shaft section is positioned within the conduit lumen such that the device end of the conduit overlaps the shaft section and where the plug-port member is located within the interior passage such that in a fill configuration, the port section and the plug section are located within the internal reservoir allowing the fluid to pass from the conduit lumen into the shaft lumen, through one or more port openings in the port section and into the internal reservoir; and
the plug-port member comprises a weakened section adjacent to the plug section, wherein pulling the fill end of the conduit applies a pulling force on the shaft section such that once the pulling force exceeds a frictional resistance force between the plug-port member and the anchor structure, the plug-port member seats into the anchor structure such that the port section is no longer in fluid communication with the internal reservoir, wherein once seated into the anchor structure, continued application of the pulling force causes detachment of the shaft section from the plug section at the weakened section to permit detachment of the conduit from the device body.

2. The medical device of claim 1, wherein the anchor structure is located interior to the internal reservoir.

3. The medical device of claim 1, wherein the anchor structure is located exterior to the internal reservoir.

4. The medical device of claim 1, wherein the shaft section is completely located interior to the internal reservoir.

5. The medical device of claim 1, wherein the shaft section is located at least in part exterior to the internal reservoir.

6. The medical device of claim 1, wherein the plug-port member comprises a higher elastic modulus than an elastic modulus of the conduit such that the conduit stretches during application of the pulling force, prior to the pulling force exceeding the frictional resistance force to store an energy to seat the plug-port member into the anchor structure while the device body is restrained.

7. The medical device of claim 1, wherein the conduit is inelastic and transmits a pulling force to seat the plug-port member into the anchor structure while the device body is restrained.

8. The medical device of claim 1, wherein the weakened section is between the device end and the one or more port openings.

9. The medical device of claim 1, wherein the weakened section is formed at the one or more port openings.

10. The medical device of claim 1, wherein the weakened section is between the fill end and the one or more port openings.

11. The medical device of claim 1, further comprising a radiopaque marker positioned concentric to the anchor structure.

12. The medical device of claim 1, wherein the plug-port member is monolithic.

13. A valve assembly for use with an expandable device body, the valve assembly comprising;
an anchor structure affixed to a wall of the device body and having an interior passage;
a conduit having a fill end and a device end with a conduit lumen extending therethrough;
a plug-port member comprising a shaft section opposite to a plug section, with a port section located therebetween, wherein the shaft section comprises a shaft lumen in fluid communication with the port section, where the shaft section is positioned within the conduit lumen such that the device end of the conduit is coupled to the shaft section and where the plug-port member is located within the interior passage such that in a fill configuration, the port section and the plug section are located within an internal reservoir of the expandable device body allowing the fluid to pass from conduit lumen into the shaft lumen, through one or more port openings in the port section and into the internal reservoir; and
the plug-port member comprises a weakened section adjacent to the plug section, wherein pulling the fill end of the conduit applies a pulling force on the shaft section such that once the pulling force exceeds a frictional resistance force between the plug-port member and the anchor structure, the plug-port member seats into the anchor structure such that the port section is no longer in fluid communication with the internal reservoir, wherein once seated into the anchor structure, continued application of the pulling force causes detachment of the shaft section from the plug section at the weakened section to permit detachment of the conduit from the expandable device body.

14. The valve assembly of claim 13, wherein the anchor structure is located interior to the internal reservoir.

15. The valve assembly of claim 13, wherein the anchor structure is located exterior to the internal reservoir.

16. The valve assembly of claim 13, wherein a portion of the anchor structure is exterior to the device body.

17. The valve assembly of claim 13, further comprising a sealing ring positioned inside the interior passage.

18. The valve assembly of claim 13, wherein the plug-port member comprises a higher modulus than a modulus of the conduit such that the conduit stretches during application of the pulling force to store an energy to seat the plug-port member into the anchor structure while the device body is restrained.

19. The valve assembly of claim 13, wherein the conduit is configured to stretch during application of the pulling force, where the stretching of the conduit builds a force to seat the plug-port member into the anchor structure while the device body is restrained.

20. The valve assembly of claim 13, wherein the weakened section is between the device end and the one or more port openings.

21. The valve assembly of claim 13, wherein the weakened section is formed at the one or more port openings.

22. The valve assembly of claim 13, wherein the weakened section is between the fill end and the one or more port openings.

23. The valve assembly of claim 13, further comprising a radiopaque marker positioned concentric to the plug-port member at the plug section.

24. An implantable medical device comprising:
- a device body having an internal reservoir and configured to expand in size upon delivery of a fluid into the internal reservoir;
- an anchor structure affixed to a wall of the device body and having an interior passage;
- a conduit having a fill end and a device end with a conduit lumen extending therethrough;
- a plug-port member comprising a shaft section opposite to a plug section, with a port section located therebetween, wherein the shaft section comprises a shaft lumen in fluid communication with the port section, where the shaft section is positioned within the conduit lumen such that the device end of the conduit overlaps the shaft section such that the shaft section is within the conduit, where the plug-port member is located within the interior passage such that in a fill configuration, the port section and the plug section are located within the internal reservoir allowing the fluid to pass from the conduit lumen into the shaft lumen, through one or more port openings in the port section and into the internal reservoir; and
- wherein the device end of the conduit comprises a weakened section, the weakened section dividing the device end of the conduit into a residual section and a removable section, the residual section disposed adjacent to the shaft section, wherein pulling the fill end of the conduit causes detachment of the removable section from the residual section at the weakened section to permit detachment of the conduit from the device body.

25. The medical device of claim 24, wherein after detachment of the conduit, the residual section is entirely within the anchor structure.

26. The medical device of claim 24, wherein the weakened section is between the fill end and the port section.

27. An implantable medical device comprising:
- a device body having an internal reservoir and configured to expand in size upon delivery of a fluid into the internal reservoir;
- an anchor structure affixed to a wall of the device body and having an interior passage;
- a conduit having a fill end and a device end with a conduit lumen extending therethrough;
- a plug-port member comprising a shaft section opposite to a plug section, with a port section located therebetween, wherein the shaft section comprises a shaft lumen in fluid communication with the port section, where the shaft section is positioned within the conduit lumen such that the device end of the conduit overlaps the shaft section and where the plug-port member is located within the interior passage such that in a fill configuration, the port section and the plug section are located within the internal reservoir allowing the fluid to pass from the conduit lumen into the shaft lumen, through one or more port openings in the port section and into the internal reservoir; and
- a weakened section located between the fill end and the plug section, wherein pulling the fill end of the conduit causes breaking of the weakened section, wherein the conduit and the shaft section break away from the port section after the plug-port member is pulled into the anchor structure.

28. The medical device of claim 27, wherein the weakened section is on the shaft section of the plug-port member.

29. The medical device of claim 27, wherein the weakened section is on the conduit.

* * * * *